US006878737B2

(12) United States Patent
Rabindran et al.

(10) Patent No.: US 6,878,737 B2
(45) Date of Patent: Apr. 12, 2005

(54) REVERSAL OF MULTIDRUG RESISTANCE IN HUMAN COLON CARCINOMA CELLS

(75) Inventors: Sridhar Krishna Rabindran, Chestnut Ridge, NY (US); Haiyin He, Washington Township, NJ (US); Lee Martin Greenberger, Montclair, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 127 days.

(21) Appl. No.: 10/086,132

(22) Filed: Feb. 28, 2002

(65) Prior Publication Data

US 2002/0169111 A1 Nov. 14, 2002

Related U.S. Application Data

(62) Division of application No. 09/321,182, filed on May 27, 1999, now Pat. No. 6,372,775.
(60) Provisional application No. 60/109,801, filed on May 27, 1998.

(51) Int. Cl.[7] .......................... A01N 31/40; A01N 43/38; A01N 43/42

(52) U.S. Cl. ....................... 514/410; 514/411; 514/415; 514/279; 514/280

(58) Field of Search ................................ 514/410, 411, 514/415, 279, 280

(56) References Cited

U.S. PATENT DOCUMENTS 5,387,685 A     2/1995  Powell et al.

OTHER PUBLICATIONS

Cole, R.J., and Cox, R.H., Tremorgen Group, in Handbook of Toxic Fungal Metabolites, 1981, Academic Press, New York, 355–367.
Durr, E E et al. Cancer Treat. Rev., 10, 3–11, 1983.
Bhalla, K. et al, Cancer Res., 45, 3657–3662, 1985.
D.M. Harrison et al., Tetrahedron Letters, vol. 27, No. 4, pp. 521–524, 1986.
M. Nakagawa et al., Tetrahedron Letters, vol. 27, No. 28, pp. 3235–3238, 1986.
Batist, G., et al, J.Biol. Chem., 261, 15544–15549, 1986.
R. Plante et al., J. Org. Chem. 1987, 52, 560–564.
Hindenburg, A.A., et al, Cancer Res., 47, 1421–1425, 1987.
Greenberger, L.M., et al, J.Biol.Chem., 262, 13685–13689, 1987.
Gruber, A. et al., Int. J. Cancer, 41, 224–226, 1988.
Kramer, R.A. et al, Science, 24(1), 694–697, 1988.
Dalton, W.S., et al, Cancer Res., 48, 1882–1888, 1988.
S. Kodato et al., Tetrahedron, vol. 44, No. 2, pp. 359–377, 1988.

Young, R.C. Drug resistance; the clinical problem, in Drug Resistance in Cancer Therapy, R.F. Ozols, Editor, Kluwer Acad. Press, Boston, 1–12, 1989.
M. Nakagawa et al., Chem. Pharm. Bull. 37(1), 23–32 (1989).
T. Hino et al., Tetrahedron, vol. 45, No. 7, pp. 1941–1944, 1989.
Goldstein, L.J. et al, J.Natl. Canc. Inst, 81, 116–124, 1989.
Lui, L.F., DNA topoisomerase posions as antitumor drugs, Annu. Rev. Biochem., 58, 351–375, 1989.
Nishiyama, M. and Kuga T., Japan J. Pharmacol., 50, 167–173, 1989.
Cole, S.P.C., et al, Br.J.Cancer, 59, 42–46, 1989.
Harker, W.C. et al, Cancer Res., 49, 4542–4549, 1989.
McGrath, T., et al, Cancer Res., 48, 3959–3963, 1989.
Ford, J.M. et al, Cancer Res., 50, 1748–1756, 1990.
Baas, R. et al, Cancer Res, 50, 5392–5398, 1990.
Ellason, J.F. et al, Int. J. Cancer, 46, 113–117, 1990.
Nishiyama, M. and Kuga T., Japan J. Pharmacol., 52, 201–208, 1990.
Chen, Y.N. et al, J. Biol. Chem., 265, 10073–10080, 1990.
Skehan, P. et al, J. Nat. Cancer Inst., 82, 1107–1112, 1990.
Dietel, M., et al. Cancer Res., 50, 6100–6106, 1990.
Rubinstein, L.V. et al, J. Nat. Cancer Inst., 82, 1113–1117, 1990.
Faulds, D., et al, Drugs, 41, 400–449, 1991.
Cowan, J.D. et al., J.Nat. Canc. Inst., 83, 1077–1084, 1991.
Taylor, C.W. et al, Br.J.Cancer, 63,923–929, 1991.
Harker, W.C. et al, Biochemistry, 30, 9953–9961, 1991.
Nakagawa, M., et al, Cancer Res., 52, 6175–6181, 1992.
Chabner, B.A., Campothecins, J.Clin.Oncol., 10, 3–4, 1992.
Versantvoort, C.H.M., et al, Br.J.Cancer, 68, 939–946, 1993.
Gottesman, M.M. and Pastan, I., Annu. Rev. Biochem, 62, 385–427, 1993.
Arceci, R.J., Blood, 81, 2215–2222, 1993.
Scheper, R.J. et al, Cancer Res., 53, 1475–1479, 1993.
Arceici, R.J. et al., Cancer Res., 53, 310–317, 1993.
Greenberger, L.M., et al., In Vitro Models of Multiple Drug Resistanc and L.J. Goldstein and R.F. Ozols, Editor Kluwer Academic Publishers, Norwell, MA, 69–106, 1994.
Sikic, B.I., et al, J. Clinical Reversal of Multidrug Resistance in Anticancer Drug Resistance, L.J. Goldstein and R.F. Ozols, Editor.
Kluwer Academic Publishers, Norwell, MA 149–165, 1994.
Zhang, X.P., et al, Oncol. Res., 6, 291–301, 1994.
Cole, S.P.C., et al. Cancer Res., 54, 5902–5910, 1994.
Zaman, C.J.R., et al, Proc. Natl. Acad. Sci. USA, 91, 8822–8826, 1994.
Jedlitschky, G. et al, Cancer Res., 54, 4833–4836, 1994.
Futscher, B.W. et al, Biochem. Pharmacol., 47, 1601–1606, 1994.

(Continued)

Primary Examiner—Jezia Riley
(74) Attorney, Agent, or Firm—Daniel B. Moran

(57) ABSTRACT

The present invention describes the use of fumitremorgin A, B and C and a series of diketopiperazines of Formula (I) to resensitize multidrug resistant (MDR) cancer cells to the cytotoxic effects of chemotherapeutic drugs.

9 Claims, No Drawings

OTHER PUBLICATIONS

Flens, M.J. et al, Cancer Res., 54, 4557–4563, 1994.
Leier, I., et al, J. Biol.Chem, 269, 27807–27810, 1994.
Abe, T., et al, Br.J.Cancer, 72, 418–423, 1995.
Tasanki, Y., et al., J. Urology, 154, 1210–1216, 1995.
Gekeler, V., et al, Biochem. Biophs. Res. Commun., 206, 119–126, 1995.
Goldstein, L.J., Current Prob. Cancer, 19, 65–124, 1995.
Brock, I., et al, Cancer Res., 55, 459–462, 1995.
Harker, W.C. et al, Cancer Res., 55, 4962–4971, 1995.
Lois, A.F., et al, Cancer Res., 55, 4010–4013, 1995.
Yang, C.H. et al, Cancer Res., 55, 4004–4009, 1995.
Bow, E.J., J. Clin. Oncol., 14, 1345–1352, 1996.
Tannock, I.F., J. Clin. Oncol., 14, 1756–1764, 1996.
Loe, D.W., et al, European J. Cancer, 32A, 945–957, 1996.
Greenberger, L.M., et al, Oncol. Res., 8, 207–218, 1996.
C.B. Cui et al., Journal of Antibiotics, Jun. 1996.
T. Hino and M. Nakagawa, Heterocycles, vol. 46, 1997.
H. Wang and A. Ganesan, Tetrahedron Letters, vol. 38, No. 24, pp. 4327–4328, 1997.
O'Malley, Gerard J. et al, Tetrahedron Lett. (1987), 28(11), 1131–4.
Bailey, Patrick D., et al, Tetrahedron Lett., (1989), 30(46), 6421–2.
Bailey, Patrick D. et al, J.Chem.Soc., Perkin Trans. 1 (1993), (4), 451–8.
Cui, Cheng–Bin. et al, J. Antibiot. (1996), 49(6), 527–533.
Cui, Cheng–Bin, et al, Tetrahedron (1996), 52(39), 12651–12666.
Cui, Cheng–Bin, et al, Tennen Yuki Kagobutsu Toronkai Koen Yoshishu (1996), 38$^{th}$, 49–54.
Cui, Cheng–Bin, et al, Tennen Yuki Kagobutsu Toronkai Koen Yoshishu (1996), 38$^{th}$, 49–54. (English Abstract).
Rabindran, Sridhar K.; Cancer Res. Alert; 2, (2), 19–21, Jul. (2000).

REVERSAL OF MULTIDRUG RESISTANCE IN HUMAN COLON CARCINOMA CELLS

This application is a of application Ser. No. 09/321,182, filed May 27, 1999 now U.S. Pat. No. 6,372,775 which claims benefit of prior U.S. Provisional application No. 60/109,801 which was converted from U.S. patent application Ser. No. 09/085,549 filed May 27, 1998, pursuant to a petition filed under 37C.F.R. 1.53(C)(2) on Nov. 2, 1998. These applications are herein incorporated by reference in their entireties.

BACKGROUND OF THE INVENTION a) Field of the Invention

The present invention describes the use of fumitremorgin A, B and C and a series of diketopiperazines of Formula (I) to resensitize multidrug resistant (MDR) cancer cells to the cytotoxic effects of chemotherapeutic drugs.

b) Description of the Prior Art

Resistance of tumor cells to chemotherapeutic drugs is a serious problem in the clinical management of cancer and reversal of resistance is a major goal in cancer chemotherapy. One type of resistance is characterized by the cross resistance to a wide variety of chemotherapeutic agents having no major structural similarities or similar modes of action. This phenomenon is termed multiple drug resistance. Multiple drug resistance (MDR) may be due to the presence of P-glycoprotein (P-gp), a transmembrane protein member of the ATP-binding cassette transporter (ABC transporter) family of proteins. P-gp acts as a drug efflux pump and actively transports chemotherapeutic agents out of the cells and thereby lowers the intracellular concentrations of such drugs to non-toxic, i.e., ineffective, levels. Chemotherapeutic drugs or agents (also used interchangeably herein as anticancer agent, antitumor agent and chemotherapy, in clinical use for the treatment of cancer to which multiple drug resistance has been observed include mitoxantrone, doxorubicin, vinblastine, vincristine, paclitaxel, daunomycin, etoposide, teniposide and actinomycin D. Inhibition of this drug efflux pump by pharmacological agents has been shown to reverse resistance and resensitize resistant cells to antitumor agents. In the early 1980's it was discovered that some multiple drug resistant tumor cells could be resensitized to chemotherapeutic agents with verapamil and with trifluoroperizine. Although P-gp is expressed in up to 50% of human tumors, several lines of evidence in the laboratory and in cancer patients suggest that P-gp alone does not account for all forms of multidrug resistance.

Mitoxantrone is an important anticancer drug with therapeutic efficacy similar to that of standard induction and salvage regimens in non-Hodgkin's lymphoma, a variety of leukemias, advanced breast cancer, and for palliative therapy in advanced prostate cancer. Like doxorubicin, it is a multi-ring planar molecule that intercalates with DNA. However, it can be distinguished from doxorubicin based on its mechanism of action, its reduced cardiotoxicity compared to anthracyclines, and its mechanism of resistance. In particular, resistance to doxorubicin and mitoxantrone involve transporters with overlapping but distinct specificities. For example, cells expressing P-gp are often cross-resistant to mitoxantrone and doxorubicin, and both molecules are efficiently transported by this protein. However, a second ABC transporter, the multidrug resistance protein (MRP), is induced by, and can mediate resistance to, doxorubicin but not mitoxantrone.

Selection of cells in mitoxantrone, doxorubicin or the podophyllotoxins often result in drug resistant sublines in which P-gp levels remain low or absent. Here, MDR is associated with decreased drug accumulation, altered intracellular trafficking, alterations in the activity/levels of topoisomerase II or changes in glutathione metabolism. In addition, multiple changes may exist together within the drug resistant cell, and a switch in the resistance mechanism from non P-gp to P-gp mediated MDR may occur as a cell line is cultured in increasing concentration of the selective agent.

Selection of tumor cells for resistance to mitoxantrone frequently results in a characteristic phenotype that has been found in human tumors derived from diverse tissue types, including colon (WiDr and LS174T), breast (MCF-7), myeloid (8226), and gastric (EGP85). The primary phenotypic feature is profound resistance to mitoxantrone, moderate resistance to related anthracycline molecules (doxorubicin and bisantrene), and little or no cross-resistance to camptothecin or to the microtubule-active drugs vinblastine, paclitaxel, and colchicine. Overexpression of two putative drug efflux pumps, P-gp or MRP, is generally not observed. Recently, a third ABC transporter, known as breast cancer resistance protein (BCRP), mitoxantrone resistance gene (MXR), or placenta-specific ABC gene (ABCP), has been reported to induce, and mediate resistance to, mitoxantrone, doxorubicin, and topotecan.

Fumitremorgin A, B and C are tremorgenic mycotoxins isolated from *Aspergillus fumigatus* and have been reported as interesting synthetic targets (T. Hino and M. Nakagawa, Heterocycles 46, 673–704(1997); C. Cui, H. Kakeya and H. Osada, J. of Antibiotics, 49(6), 534–540(1996); M. Nakagawa et al, Tetrahedron Let. 27(28), 3235–3238(1986); S. Kodato et al, Tetrahedron, 44(2), 359–377(1988); and D. M. Harrison and R. B. Sharma, Tetrahedron Let., 27, 521 (1986)) and have not been previously reported to resensitize multidrug resistant (MDR) cancer cells to the cytotoxic effects of anticancer agents.

SUMMARY OF THE INVENTION

By selecting human colon carcinoma S1 cells, a subclone of LS174T cells, which survive in increasing concentrations of up to 3.2 $\mu$M of mitoxantrone, the multiple drug resistant human colon carcinoma cell line S1-M1-3.2 was obtained. This multiple drug resistant phenotype which is not reversed by verapamil or the potent P-gp inhibitor α-(3,4-dimethoxyphenyl)-3,4-dihydro-6,7-dimethoxy-α-[(4-methylphenyl)thio]-2(1H)-isoquinolineheptanenitrile (U.S. Pat. No. 5,387,685) is dependent in part upon an energy-dependent drug efflux mechanism. P-gp and the multiple drug resistance protein (MRP) are not elevated in the mitoxantrone resistant cells relative to the drug sensitive parent, suggesting that resistance is mediated by a novel pathway of drug transport.

One aspect of this invention is to provide a cell-based assay with S1-M1-3.2 cells which can be used as a method to identify agents capable of circumventing non P-gp/non-MRP mediated MDR and identify chemosensitizing compounds which can resensitize cells to the cytotoxic effects of the chemotherapeutic drugs listed hereinabove.

An important aspect of this invention is the capability to identify test compounds as chemosensitizing agents following evaluation in an assay of this invention.

A further aspect of this invention is a method for identifying chemosensitizing compounds that reverse non P-gp/non MRP multiple drug resistance in cancer cells exhibiting non P-gp/non MRP drug resistance phenotype comprising administration of a test compound and a chemotherapeutic agent to which cancer cells are resistant and measuring cancer cell survival.

An additional feature of this invention is a method for resensitizing non P-gp/non MRP multiple drug resistant cancer cells to treatment with chemotherapeutic agents to which cancer cells have developed resistance comprising administration of an effective amount of a chemosensitizing reversal agent and a chemotherapeutic agent.

Fumitremorgin A (FTA), fumitremorgin B (FTB), fumitremorgin C (FTC) and compounds of Formula (I) were found to be active agents in a cell based assay with S1-M1-3.2 cells. Mycotoxin fumitremorgin C (FTC) identified in this assay is extremely effective in reversing resistance to mitoxantrone or doxorubicin in multiple drug-selected cell lines showing this novel phenotype. The toxic amount of FTC which kills more than 20% of the S1-M1-3.2 cells is greater than 80.0 μM. At a level of 0.3 μM, FTC plus 3.2 μM mitoxantrone causes a 50% cell kill (IC$_{50}$ 0.3 μM). In addition, FTC also reverses topotecan resistance. Reversal of resistance was associated with an increase in drug accumulation in the cell. FTC also reverses resistance, and increases drug accumulation in cells made resistant by transfection with the BCRP gene.

Another aspect of the invention is a method for identifying chemosensitizing compounds that reverse BCRP-mediated multiple drug resistance in cancer cells which exhibit BCRP-mediated multiple drug resistance comprising administration of a test compound and a chemotherapeutic agent to which the cancer cells are resistant and measuring cancer cell survival.

A further aspect of the invention is a method for resensitizing BCRP-mediated multiple drug resistant cancer cells to treatment with chemotherapeutic agents to which cancer cells have developed resistance comprising administration of an effective amount of a chemosensitizing reversal agent and a chemotherapeutic agent.

A further feature of the invention is a method of distinguishing P-gp/MRP multiple drug resistance from BCRP or other non-P-gp/non MRP multiple drug resistance which comprises administration of an effective amount of a chemosensitizing reversal agent and a chemotherapeutic agent to which cancer cells are resistant and measuring cancer cell survival.

A further aspect of the invention is a method of distinguishing P-gp/MRP multiple drug resistance from BCRP or other non-P-gp/non MRP multiple drug resistance which comprises administration of an effective amount of a chemosensitizing reversal agent and a chemotherapeutic agent to which the cancer cells are multiple drug resistant and measuring chemotherapeutic agent accumulations in the cell.

An additional feature of the invention is a method of determining the presence and magnitude of cancer cell BCRP or other non P-gp/non MNP resistance in cancer cells exhibiting such resistance which comprises administration of an effective amount of a chemosensitizing reversal agent and chemotherapeutic agents to resistant cancer cells from humans and measuring cancer cell survival.

A further feature of the invention is a method of reversing BCRP or other non P-gp/non MRP resistance to chemotherapeutic agents in a mammal which comprises administration of an effective amount of a chemosensitizing reversal agent to a mammal in need thereof having a BCRP or other non-P-gp/non MRP resistant cancer.

An additional feature of this invention is a method of treatment of BCRP or other non P-gp/non MRP multiple drug resistant phenotype cancer cells which comprises administration of an effective amount of a chemosensitizing reversal agent and a chemotherapeutic agent to which the cancer is resistant.

One more aspect of the invention is to provide a method of inhibiting efflux of a chemotherapeutic agent in a mammal in need thereof which comprises administration of an effective amount of a chemosensitizing reversal agent and a chemotherapeutic agent to which the cancer is resistant.

An additional aspect of the invention is to provide a culture of the organism *Aspergillus fumigatus* having the identifying characteristics of LL-S266, said culture being capable of producing Fumitremorgin A, B and C in recoverable quantity upon fermentation in an aqueous nutrient medium containing assimilable sources of carbon and nitrogen.

FUMITREMORGIN A (FTA)

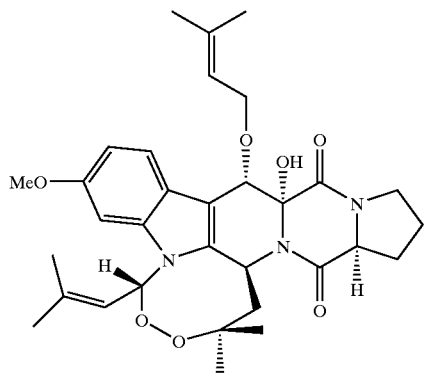

FUMITREMORGIN B (FTB)

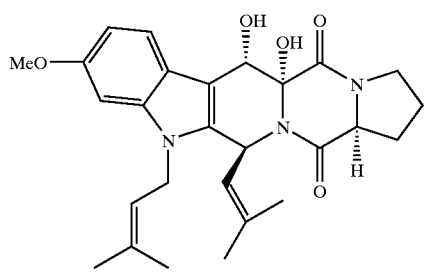

FUMITREMORGIN C (FTC)

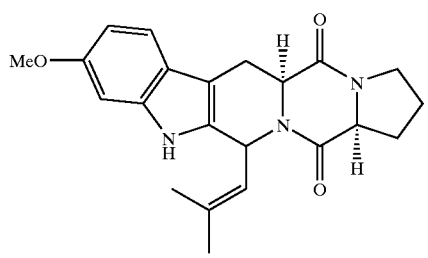

Thus, the S1-M1-3.2 human colon cancer drug resistant cell line can be used to identify compounds which reverse this non P-gp/non MRP multiple drug resistance and FTC can be used to reverse the resistance of this drug resistant phenotype and could be administered prior to, during, or after administration of antitumor drugs to reverse this resistance. FTC may also be used to identify multidrug resistant non P-gp/non MRP cancer cells due to its ability to resensitize these cancer cells to chemotherapeutic drugs.

FTC is a highly selective reagent, since it did not reverse resistance in P-gp positive S1 colon cancer LS174T cells selected with bisantrene (S1-B1-20) or MRP-positive promyelocytic leukemia cells (HL60) selected with doxorubicin (HL60/AR). Furthermore, the activity of FTC is not limited to S1-M1-3.2 cells since it reversed resistance to doxorubicin and mitoxantrone in a breast cancer cell line (MCF-7) selected for resistance to mitoxantrone, and a second MCF-7 cell line selected in doxorubicin plus verapamil. FTC also reversed low level resistance in myeloid 8226/MR4 cells selected for resistance to mitoxantrone. These findings demonstrate that the resistance pathway in the S1-M1-3.2 cells occurs in a variety of tumor types, and is not unique to colon cells. The residual resistance which is not reversed by FTC may be due to other mechanisms of resistance such as reduced topoisomerase II activity, or low expression of P-gp and MRP. Two cell lines that have not been selected for resistance to chemotherapeutic agents, a breast cell line (MCF-7), and two non small cell lung carcinoma cell lines (H460 and A549), can be sensitized to mitoxantrone by FTC. This suggests that inherent resistance to mitoxantrone may occur in some cells. FTC may be a useful tool to identify this phenotype in the absence of other markers.

This invention additionally discloses diketopiperazines of Formula (I) which were synthesized and tested for reversal of multiple drug resistance and toxicity,

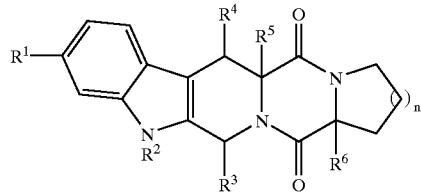

(I)

wherein:
n is an integer of 0, 1, or 2;
$R^1$ is hydrogen or alkoxy of 1 to 10 carbon atoms;
$R^2$ is hydrogen or alkenyl of 2 to 10 carbon atoms;
$R^3$ is hydrogen, alkyl of 1 to 10 carbon atoms, alkenyl of 2 to 10 carbon atoms,
$R^7NH(CH2)v$- or

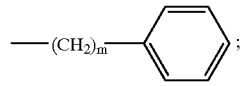

m is an integer of 1 to 6;
v is an integer of 1 to 4;
$R^4$, $R^5$ and $R^6$ are hydrogen;
$R^7$ is H or

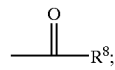

$R^8$ is selected from alkyl of 1 to 10 carbon atoms, —$(CH_2)_mCO_2H$,

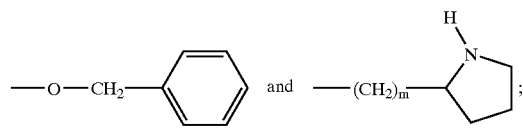

with the proviso that n is not 1 when $R^1$ is H or $CH_3O$—;
$R^2$ is H or

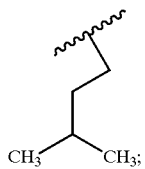

$R^3$ is

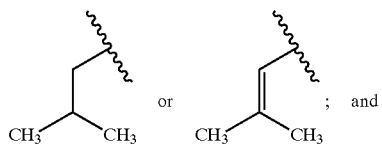

$R^4$, $R^5$ and $R^6$ are hydrogen;
or a pharmaceutically acceptable salt thereof.

Among the preferred compounds of Formula (I) of this invention are those in the subgroups, and pharmaceutically acceptable salts thereof:
a) compounds of general Formula (I)
wherein:
$R^1$ is hydrogen or alkoxy of 1 to 5 carbon atoms;
$R^2$ is hydrogen or alkenyl of 2 to 6 carbon atoms;
$R^3$ is hydrogen, alkyl of 1 to 9 carbon atoms, alkenyl of 2 to 6 carbon atoms,
$R^7NH(CH2)v$- or

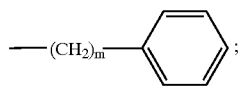

m is an integer of 1 to 5;
v is an integer of 1 to 3; and
n, $R^4$, $R^5$, $R^6$, $R^7$ and $R^8$ are hereinbefore defined;
b) compounds of general Formula (I)
wherein:
$R^3$, $R^4$ and $R^5$ are independently (R) or (S);
c) compounds of general Formula (I)
wherein:
$R^1$ is hydrogen or $CH_3O$—;
$R^2$ is hydrogen or 3-methyl-2-buten-1-yl;
$R^3$ is hydrogen or (R) or (S) 2-methylpropyl, 2-methyl-2-propenyl, nonanyl, 5-phenylpentyl, or $R^7NHCH_2CH_2CH_2$—where $R^7$ is hydrogen, acetyl, butyryl, succinoyl, or 3-(2-pyrrolidinyl)propionyl;
$R^4$ and $R^5$ independently are (R) or (S) hydrogen; and
$R^6$, $R^8$, n and v are hereinbefore defined.

Among the specifically preferred compounds of this invention according to general Formula (I) are the following compounds or pharmaceutically acceptable salts thereof:
(5aS,12R,14aR)-12-isobutyl-1,2,3,5a,6,11,12,14a-octahydro-5H,14H-pyrrolo[1",2":4',5']pyrazino[2',1':6,1]pyrido[3,4-b]indole-5,14-dione,
(5aS,12S,14aR)-12-isobutyl-1,2,3,5a,6,11,12,14a-octahydro-5H,14H-pyrrolo[1",2":4',5']pyrazino[2',1':6,1]pyrido[3,4-b]indole-5,14-dione,
(5aR,12R,14aR)-12-isobutyl-1,2,3,5a,6,11,12,14a-octahydro-5H,14H-pyrrolo[1",2":4',5']pyrazino[2',1':6,1]pyrido[3,4-b]indole-5,14-dione,
(5aR,12S,14aR)-12-isobutyl-1,2,3,5a,6,11,12,14a-octahydro-5H,14H-pyrrolo[1",2":4',5']pyrazino[2',1':6,1]pyrido[3,4-b]indole-5,14-dione,
(6aS,13R,15aS)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione, (6aS,13S,15aS)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione,
(6aR,13R,15aS)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione,
(6aR,13S,15aS)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione,
(6aS,13R,15aR)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione,
(6aS,13S,15aR)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione,
(6aR,13R,15aR)-13-isobutyl-1,2,3,4,6a,7,12,13,15a-nonahydro-6H,15H-pyrido[1",2":4',5']pyrazino[2',1':6,1]pyrido[3,4-b]indole-6H, 15H-dione,
(6aR,13S,15aR)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione,
(4aS,11R,13aS)-11-isobutyl-1,4a,5,10,11,13a-hexahydro-4H-azeto[1",2":4',5']pyrazino[2',1':6,1]pyrido[3,4-b]indole-4,13(2H)-dione,
(4aS,11S,13aS)-11-isobutyl-1,4a,5,10,11,13a-hexahydro-4H-azeto[1",2":4',5']pyrazino[2',1':6,1]pyrido[3,4-b]indole-4,13(2H)-dione,
(5aS,12R,14aS)-12-(5-phenylpentyl)-1,2,3,5a,6,11,12,14a-octahydro-5H,14H-pyrrolo[1",2":4',5']pyrazino[2',1':6,1]pyrido[3,4-b]indole-5,14-dione,
(5aS,12S,14aS)-12-(5-phenylpentyl)-1,2,3,5a,6,11,12,14a-octahydro-5H,14H-pyrrolo[1",2":4',5']pyrazino[2',1':6,1]pyrido[3,4-b]indole-5,14-dione,
benzyl 3-[(5aS,12R,14aS)-5,14-dioxo-2,3,5a,6,11,12,14,14a-octahydro-1H,5H-pyrrolo[1",2":4',5']pyrazino[2',1':6,1]pyrido[3,4-b]indol- 12-yl]propylcarbamate,
benzyl 3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propylcarbamate,
(5aS,14aS)-1,2,3,5a,6,11,12,14a-octahydro-5H,14H-pyrrolo[1",2":4',5']pyrazino[2',1':6,1]pyrido[3,4-b]indole-5,14-dione,
(5aS,12S,14aS)-12-methyl-1,2,3,5a,6,11,12,14a-octahydro-5H,14H-pyrrolo[1",2":4',5']pyrazino[2',1':6,1]pyrido[3,4-b]indole-5,14-dione,
(5aS,12S,14aS)-12-nonyl-1,2,3,5a,6,11,12,14a-octahydro-5H,14H-pyrrolo[1",2":4',5']pyrazino[2',1':6,1]pyrido[3,4-b]indole-5,14-dione,
(5aS,12R,14aS)-12-(3-aminopropyl)-1,2,3,5a,6,11,12,14a-octahydro-5H,14H-pyrrolo[1",2":4',5']pyrazino[2',1':6,1]pyrido[3,4-b]indole-5,14-dione,
(5aS,12S,14aS)-12-(3-aminopropyl)-1,2,3,5a,6,11,12,14a-octahydro-5H,14H-pyrrolo[1",2":4',5']pyrazino[2',1':6,1]pyrido[3,4-b]indole-5,14-dione,
N-{3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propyl}acetamide,
N-{3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propyl}butanamide,
4-({3-[(5aS,12S,14aS)-5,14-dioxo-2,3,5a,6,11,12,14,14a-octahydro-1H, 5H-pyrrolo[1",2":4',5']pyrazino[2',1':6,1]pyrido[3,4-b]indol-12-yl]propyl}amino)-4-oxobutanoic acid,
(2S)-N-{3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propyl}pyrrolidine-2-carboxamide and
(5aS,12S,14aS)-9-methoxy-11-(3-methylbut-2-enyl)-12-(2-methylprop-1-enyl)-1,2,3,5a,6,11,12,14a-octahydro-5H,14H-pyrrolo[1",2":4',5']pyrazino[2',1':6,1]pyrido[3,4-b]indole-5,14-dione.

For the compounds defined above and referred to herein, unless otherwise noted, the following terms are defined.

The term alkyl means a branched or unbranched, saturated aliphatic hydrocarbon radical. Examples of alkyl radicals include methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 2,2-dimethylbutyl, n-heptyl, 2-methylhexyl, and the like unless otherwise specified.

The term alkenyl means a branched or unbranched hydrocarbon radical containing at least one carbon-carbon double bond, each double bond being independently cis, trans or a nongeometric isomer.

The term alkoxy means a branched or unbranched hydrocarbon radical attached through an oxygen bridge and including for example methoxy, ethoxy, n-propoxy, isopropoxy, n-butoxy, t-butoxy and the like.

It is understood by those practicing the art that the definition of compounds of Formula (I) when $R^2$, $R^3$ and $R^8$ contain asymmetric carbons, encompass all possible stereoisomers, mixtures and regioisomers thereof which possess the activity discussed below. Such regioisomers may be obtained pure by standard separation methods known to those skilled in the art. In particular, the definition encompasses any optical isomers and diastereomers as well as the racemic and resolved enantiomerically pure R and S stereoisomers as well as other mixtures of the R and S stereoisomers and pharmaceutically acceptable salts thereof, which possess the activity discussed below. Optical isomers may be obtained in pure form by standard separation techniques or enantiomer specific synthesis. It is understood that this invention encompasses all crystalline forms of compounds of Formula (I). The pharmaceutically acceptable salts of the basic compounds of this invention are those derived from such organic and inorganic acids as: lactic, citric, acetic, tartaric, fumaric, succinic, maleic, malonic, hydrochloric, hydrobromic, phosphoric, nitric, sulfuric, methanesulfonic and similarly known acceptable acids. The pharmaceutically acceptable salts of acid compounds of this invention include calcium, potassium, magnesium, sodium and the like.

The present invention accordingly provides a pharmaceutical composition which comprises a compound of Formula (I) or fumitremorgin A, B and C of this invention in combination or association with a pharmaceutically acceptable carrier. In particular, the present invention provides a pharmaceutical composition which comprises an effective amount of a compound of this invention and one or more pharmaceutically acceptable carriers.

DESCRIPTION OF THE INVENTION

The diketopiperazines of Formula (I) were synthesized as described in Scheme 1 by Pictet-Spengler reaction of tryptophan methyl ester 1 where $R^2$ is H with an aldehyde 2a or its diethyl acetal 2b where $R^3$ is hereinbefore defined affords tetrahydro-β-carboline 3 where $R^1$ and $R^3$ are hereinbefore defined and $R^2$ is H, which was then coupled to 2,2,2-trichloroethoxy-carbonyl(Troc) protected acid chloride 4 where n is hereinbefore defined to yield an amide 5 where n, $R^1$ and $R^3$ are hereinbefore defined and $R^2$ is H. The spontaneous cyclization of amide 5 followed by reductive deprotection of the Troc groups with zinc dust resulted in the formation of the pentacyclic diketopiperazines 6 where the pairs of diastereoisomers thus obtained were separated by HPLC to afford pure compounds 7 and 8 (Scheme 1).

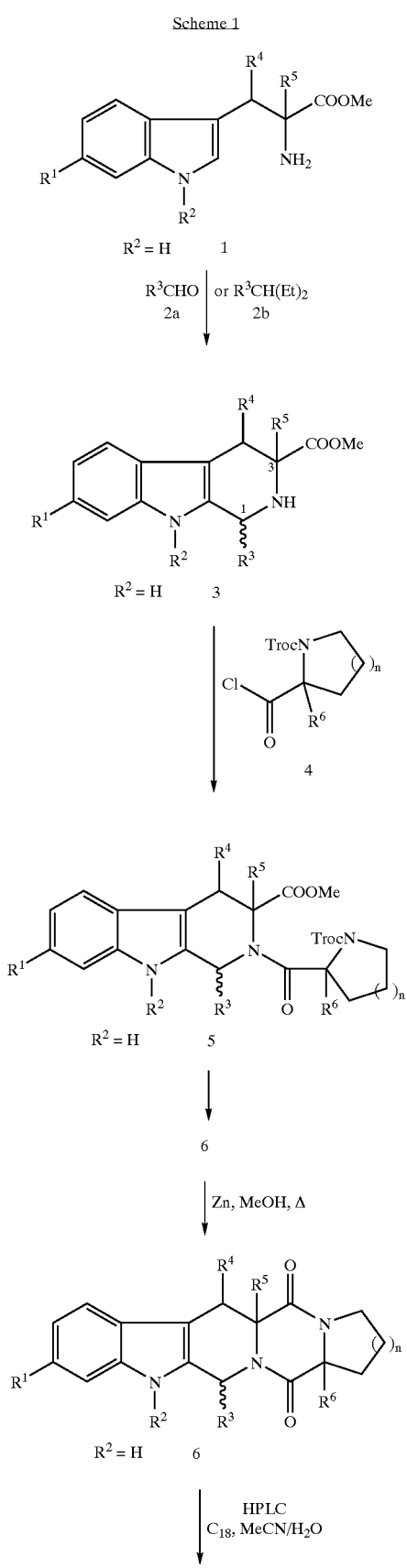
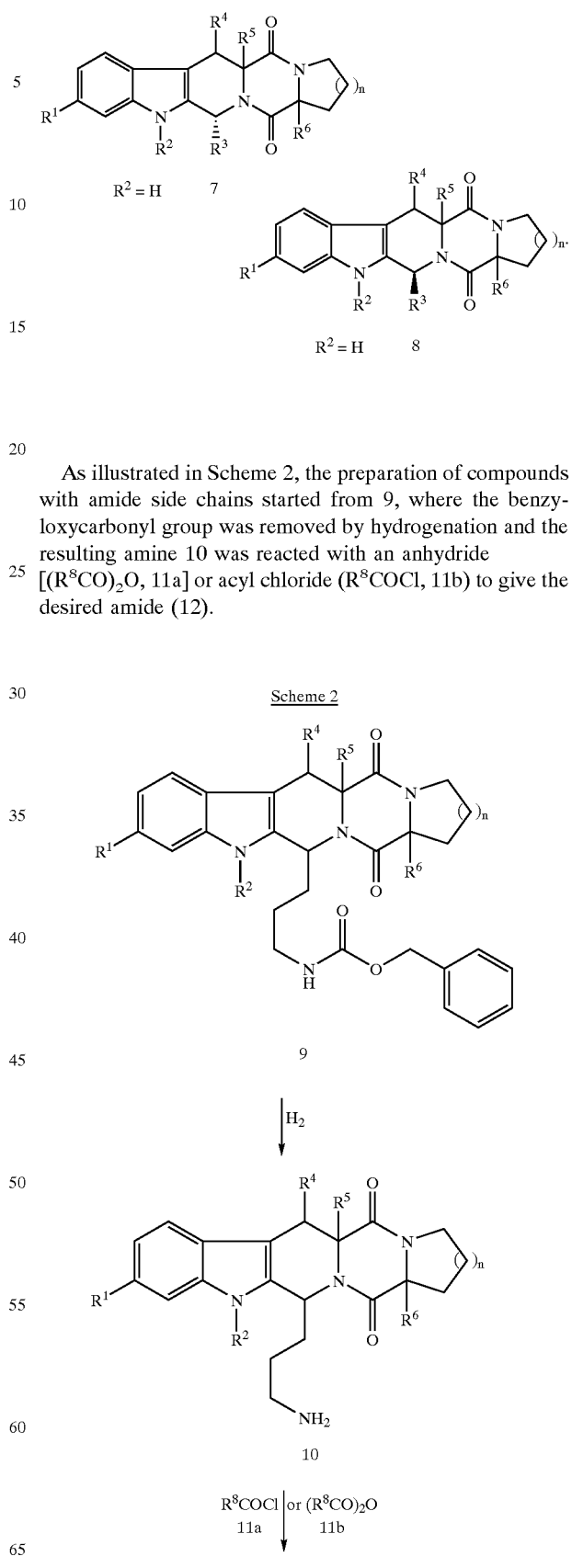
As illustrated in Scheme 2, the preparation of compounds with amide side chains started from 9, where the benzyloxycarbonyl group was removed by hydrogenation and the resulting amine 10 was reacted with an anhydride [$(R^8CO)_2O$, 11a] or acyl chloride ($R^8COCl$, 11b) to give the desired amide (12).

-continued

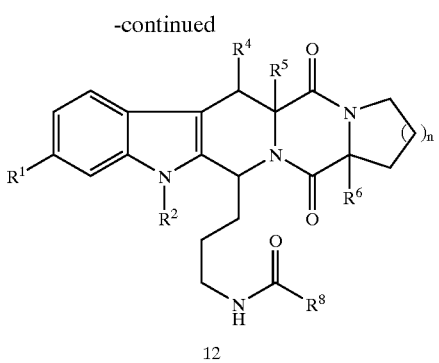

12

The fumitremorgin C 13 was alkylated to give 14 by reacting with 3,3-dimethyl allyl bromide in the presence of sodium hydride.

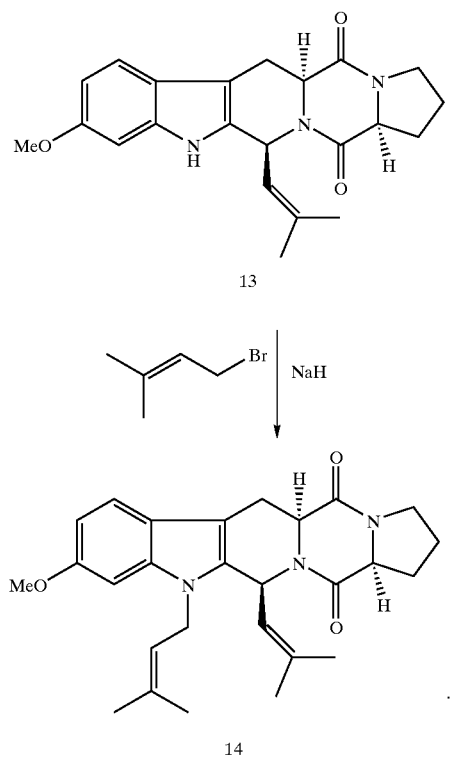

Scheme 3

Reactions are performned in a solvent appropriate to the reagents and materials employed and suitable for the transformation being effected. It is understood by those skilled in the art of organic synthesis that the various functionalities present on the molecule must be consistent with the chemical transformations proposed. This may necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray crystallography.

According to a further aspect of the present invention there is provided a series of compounds of Formula (I) or the pharmaceutically acceptable salts thereof as defined hereinbefore for use in a method of treatment of human or animal disease.

The compounds of this invention resensitize multidrug resistant (MDR) cancer cells to the cytotoxic effects of chemotherapeutic drugs and this activity was established using standard pharmacological test procedures with representative compounds of this invention as follows.

Determination of Mechanism of Resistance

The resistance of mitoxantrone-selected S1-M1-3.2 cells to various chemotherapeutic drugs is shown in Table 1. Cells were cultured for three days in the presence of the antitumor agent (triplicate points per dose). Following a 3-day growth period, cells were fixed in 10% trichloroacetic acid (TCA) for 1 hour, washed extensively with water, and cell-associated protein was stained using 0.1% sulforhodamine B (SRB), a protein binding reagent [Rubinstein et al., Journal of the National Cancer Institute 82, 1113–1118 (1990) and Skehan et al., Journal of the National Cancer Institute 82, 1107–1112 (1990)]. Excess reagent was removed by washing plates in 5% acetic acid, the dye was solubilized in 10 mM Tris base, and absorbance determined in a UV Max spectrophotometer (Molecular Devices, Menlo Park, Calif.) at 540 nm. Cell survival was estimated relative to control wells (no drugs). $EC_{50}$ values ($\mu$M) were estimated from cytotoxicity curves. For S1, the values shown [mean±SE (number of independent observations)] are taken from Zhang et al., "P-Glycoprotein Mediates Profound Resistance to Bisantrene," Oncol. Res., 6:291–301, 1994. Values for S1-M1-3.2 are compiled from 2–7 independent experiments.

TABLE 1

Resistance profile of mitoxantrone-selected cells.

| Antitumor Agent | S1 ($EC_{50}$) | S1-M1-3.2 (relative resistance) |
| --- | --- | --- |
| mitoxantrone | 28.7 ± 7.1 (8) | 1435 |
| doxorubicin | 111 ± 21.2 (9) | 54 |
| bisantrene | 528 ± 85.2 (6) | 24 |
| vinblastine | 4.4 ± 1.0 (6) | 3 |
| paclitaxel | 18.6 ± 3.3 (7) | 6 |
| colchicine | 26.1 ± 2.2 (3) | 3 |
| m-AMSA | 606 ± 147 (7) | 11 |
| etoposide | 6415 ± 1310 (5) | 6 |
| VM-26 | 662 ± 134 (4) | 18 |
| topotecan | 38.8 ± 30.6 (2) | 41 |
| camptothecin | 23.5 ± 15.9 (2) | 2 |

S1-M1-3.2 cells show profound resistance to mitoxantrone, with lower levels of resistance to the related anthraquinones, doxorubicin and bisantrene, and the topoisomerase I poison, topotecan. Weak, or no cross resistance was observed for the microtubule-active agents (paclitaxel, colchicine, vinblastine), and other topoisomerase poisons [camptothecin, m-AMSA, etoposide, and teniposide (VM-26)].

To determine the mechanism of resistance, drug resistant and sensitive cells were incubated with radioactive analogues of antitumor agents and cell-associated radioactivity was measured by scintillation counting. Alternatively, surrogates of chemotherapeutic drugs may be used. The surrogate has no antitumor activity itself but interacts with the cancer cell proteins such as P-gp or MRP in a similar manner as an anticancer drug. The surrogate chemotherapeutic drug would have a property such as fluorescence which is useful for determining the drug resistance mechanisms such as efflux.

Cells were plated in 60 mm dishes ($1 \times 10^6$ cells per dish) or in 24 well clusters ($2 \times 10^5$ cells per well) and allowed to grow for 1–2 days. The cells were washed and incubated in serum-free medium containing radioactive drug for 2–4 hours at 37° C. Drugs used were [$^{14}$C]-mitoxantrone (Amersham, 1 or 5 $\mu$M; specific activity 66 mCi/mmol) or [$^{14}$C]-doxorubicin (Amersham, 0.5 or 3 $\mu$M; specific activity 50–62 mCi/mmol ). For experiments using 3 $\mu$M doxorubicin, 1.8 $\mu$M unlabeled drug was combined with 1.2 $\mu$M [$^{14}$C]-labeled drug. Unbound drug was removed by washing twice in ice-cold phosphate buffered saline (PBS), cells were solubilized in 2 N NaOH at 37° C. for 1–2 hours, and analyzed by scintillation counting. Results were normalized to cell protein content measured by a Lowry assay.

As shown in Table 2, drug sensitive (S1) and drug resistant cells (S1-M1-3.2 and S1-B1–20) were incubated in medium containing [$^{14}$C] mitoxantrone or [$^{14}$C] doxorubicin, for 90 minutes at 37° C. The cells were then washed, solubilized, and counted in a scintillation counter. Values are mean disintegration per minute per $\mu$g protein of triplicate determinations±standard deviation.

TABLE 2

Drug Accumulation Analysis

| | Drug Accumulation (DPM/$\mu$g protein) | | | |
|---|---|---|---|---|
| | Mitoxantrone | | Doxorubicin | |
| Cell Line | no FTC | with 1 $\mu$M FTC | no FTC | with 1 $\mu$M FTC |
| S1 | 2430 ± 252 | 2246 ± 233 | 114 ± 11 | 111 ± 15 |
| S1-M1-3.2 | 996 ± 57 | 2220 ± 147 | 19 ± 3 | 65 ± 17 |
| S1-B1-20 | 1086 ± 100 | 1189 ± 53 | 23 ± 1 | 26 ± 1 |

S1-M1-3.2 cells accumulated only 41% of mitoxantrone and 17% of doxorubicin compared with the parental cells. A similar decrease was seen in the P-gp expressing S1-B1-20 cells.

In order to determine whether this reduced accumulation was due to increased clearance of the drug from the cells, parental cells (S1) and drug resistant cells (S1-M1-3.2, and S1-B1-20) were loaded with [$^{14}$C] mitoxantrone for 4 hours at 37° C., washed, and incubated in medium without drug (Table 3). Cell-associated radioactivity was measured at the indicated times. Values are mean percentage of drug remaining (triplicate determinations)±standard deviation.

TABLE 3

Drug efflux analysis

| | % mitoxantrone remaining over time (hours) | | | | |
|---|---|---|---|---|---|
| Cell Line | 0 | 0.5 | 1 | 2 | 4 |
| S1 | 100 ± 6 | 99 ± 17 | 101 ± 3 | 100 ± 11 | 95 ± 13 |
| S1-M1-3.2 | 100 ± 2 | 51 ± 6 | 44 ± 1 | 45 ± 3 | 31 ± 2 |
| S1-B1-20 | 100 ± 5 | 58 ± 4 | 45 ± 10 | 41 ± 3 | 39 ± 3 |

As shown in Table 3, the amount of radioactivity remaining in the parental S1 cells decreased marginally from 100% to 95% over a four hour period, while the amount in the S1-M1-3.2 cells decreased to 31% in the same period. P-gp expressing S1-B1-20 cells also showed a similar decrease (to 39%).

To examine whether this drug efflux was energy dependent, the effect of the metabolic inhibitors sodium azide and 2,4-dinitrophenol on drug transport (Table 4) was examined. During the efflux period, cells were incubated in growth medium, PBS, PBS supplemented with sodium azide or sodium azide and 2,4-dinitrophenol. After 1 hour, cells were prepared for analysis by scintillation counting. Values shown are mean percentage of drug remaining (triplicate determinations) ± standard deviation.

TABLE 4

Effect of energy depletors on drug efflux

| | % mitoxantrone remaining in cell line | | |
|---|---|---|---|
| Treatment | S1 | S1-M1-3.2 | S1-B1-20 |
| Growth medium | 100 ± 17 | 100 ± 20 | 100 ± 14 |
| PBS | 119 ± 13 | 99 ± 8 | 114 ± 11 |
| PBS + sodium azide | 137 ± 14 | 285 ± 43 | 217 ± 6 |
| sodium azide + 2,4-dinitrophenol | 110 ± 6 | 226 ± 32 | 246 ± 25 |

In contrast with the modest increase (1.1–1.4-fold) seen in the S1 cells by these treatments, the S1-M1-3.2 cells showed a 2.1- to 2.5-fold increase, similar to that seen in the S1-B1–20 cells (2.3–2.6 fold).

Since the drug resistant cells showed low but detectable resistance to the topoisomerase II poisons m-AMSA (amsacrine), etoposide and teniposide (VM-26, Table 1), topoisomerase II activity was determined by examining the ability of nuclear extracts to decatenate *Crithedia. fasiculata* kinetoplast DNA.(Zhang et al., "P-Glycoprotein Mediates Profound Resistance to Bisantrene," Oncol. Res., 6:291–301, 1994). The amount of nuclear extract (in $\mu$g) for 50% decatenation of kinetoplast DNA is shown in Table 5.

TABLE 5

Topoisomerase II Activity in Nuclear Extracts.

| Cell line | 50% activity ($\mu$g) | Relative activity |
|---|---|---|
| S1 | 0.5 ± 0.2 | 12 |
| S1-M1-3.2 | 6.0 ± 1.6 | 1 |

A 12-fold decrease in activity was seen in the S1-M1-3.2 cells compared with the parental cells. This decrease in enzyme activity correlated with a decrease in the amount of topoisomerase II$\beta$, message and protein levels. No significant alterations were observed for topoisomerase II$\alpha$ mRNA or protein.

Identification of Reversal Agents

A variety of pharmacological agents have been shown to resensitize P-gp expressing cells to antitumor drugs in vitro. One of the first reported molecules with reversing activity was verapamil, a calcium channel blocker. However, $\alpha$-(3, 4-dimethoxyphenyl)-3,4-dihydro-6,7-dimethoxy-$\alpha$-[(4-methylphenyl)thio]-2(1H)-isoquinolineheptanenitrile (U.S. Pat. No. 5,387,685) is at least 10-fold more potent than verapamil. An experiment was carried out to determine whether veraparnil and $\alpha$-(3,4-dimethoxyphenyl)-3,4-dihydro-6,7-dimethoxy-$\alpha$-[(4-methylphenyl)thio]-2(1H)-isoquinolineheptanenitrile had reversal activity in the S1-M1-3.2 cell lines. Cells were plated into 96-well dishes (100 $\mu$l/well) in growth medium supplemented with 5% FBS. After 4–6 hours, 100 $\mu$l of the appropriate dose of mitoxantrone (at 2x) was added with the candidate reversal agent. The final concentration of mitoxantrone was the same as that used for routine culture of the cells (3.2 $\mu$M).

Reversal agents were tested from 0.1–80 μM (triplicate points per dose). In parallel wells, cells were grown in the presence of the reversal agent alone.

As shown in Table 6, cells were incubated with verapamil or α-(3,4-dimethoxyphenyl)-3,4-dihydro-6,7-dimethoxy-α-[(4-methylphenyl)thio]-2(1H)-isoquinolineheptanenitrile (or its HCl salt), alone or combined with mitoxantrone. The Difference Score is the difference in the percentage of cells surviving when the drug was given alone minus the percentage of cells surviving when the drug was given along with the antitumor agent. Values shown are mean ± standard deviation from two independent experiments.

TABLE 6

Effect of P-gp reversal agents in S1-M1-3.2 cells

| Drug (μM) | Per Cent Survival Alone | Per Cent Survival with 3.2 μM mitoxantrone | Difference Score |
|---|---|---|---|
| Verapamil | | | |
| 0.1 | 100 ± 1 | 98 ± 0 | 2 |
| 0.5 | 99 ± 1 | 98 ± 1 | 1 |
| 1 | 97 ± 2 | 98 ± 1 | −1 |
| 5 | 98 ± 5 | 97 ± 0 | 1 |
| 10 | 103 ± 4 | 94 ± 0 | 9 |
| 20 | 99 ± 4 | 93 ± 2 | 6 |
| 40 | 93 ± 6 | 83 ± 3 | 10 |
| 80 | 80 ± 24 | 58 ± 4 | 22 |
| Alpha-(3,4-di-Methoxyphenyl)-3,4-dihydro-6,7-dimethoxy-alpha-[(4-methylphenyl)thio]-2(1H)-isoquinolineheptanenitrile | | | |
| 0.1 | 98 ± 2 | 98 ± 2 | 0 |
| 0.5 | 100 ± 0 | 98 ± 0 | 2 |
| 1 | 101 ± 1 | 99 ± 2 | 2 |
| 5 | 78 ± 8 | 63 ± 8 | 15 |
| 10 | 39 ± 18 | 36 ± 11 | 3 |
| 20 | 21 ± 13 | 21 ± 10 | 0 |
| 40 | 16 ± 5 | 16 ± 4 | 0 |
| 80 | 13 ± 1 | 13 ± 2 | 0 |

The difference between cell survival for each agent (at multiple concentrations) in the absence and presence of mitoxantrone was small and occurred at concentration of candidate reversal agents that were toxic by themselves. Therefore, no significant reversal activity of these compounds in the S1-M1-3.2 cells was found.

To identify molecules that can resensitize the mitoxantrone-selected cells to anticancer drugs, extracts (1:50–1:5000 dilution) from fermentations which had little or no toxicity by themselves, but, which when combined with mitoxantrone showed substantially increased cell death were analyzed further. Using this test procedure, an extract from a solid-medium fermentation broth of *Aspergillus fumigatus* was found to be highly active. Further analysis revealed that FFA, FTB and FTC were present and separated by chromatography.

The ability of FTC to resensitize S1-M1-3.2 cells to mitoxantrone was tested. As shown in Table 7, cells were incubated for three days with the indicated doses of FTC alone or in combination with 3.2 μM mitoxantrone. Cell survival was estimated using the Sulforhodamine (SRB) assay. Values are mean±standard deviation from two independent experiments.

TABLE 7

Effect of FTC on S1-M1-3.2 cells.

| Drug (μM) | Per Cent Survival Alone | Per Cent Survival with 3.2 μM mitoxantrone | Difference Score |
|---|---|---|---|
| Fumitremorgin C | | | |
| 0.1 | 105 ± 4 | 95 ± 4 | 10 |
| 0.5 | 105 ± 2 | 39 ± 10 | 66 |
| 1 | 103 ± 1 | 30 ± 1 | 73 |
| 5 | 99 ± 5 | 24 ± 4 | 75 |
| 10 | 99 ± 1 | 22 ± 6 | 77 |
| 20 | 104 ± 4 | 17 ± 10 | 87 |
| 40 | 108 ± 5 | 14 ± 11 | 94 |
| 80 | 94 ± 4 | 13 ± 11 | 81 |

No toxicity of FTC alone was observed in the dose range tested (0.1–80 μM). However, in combination with mitoxantrone, 50% of the cells were killed with 0.35 μM of the drug. Two analogues of FTC occurring naturally in the same extract, fumitremorgin A (FTA) and B, were tested for reversal activity (Table 8). Cells were incubated for three days with the indicated doses of FTA or FTB; either alone, or in combination with 3.2 μM mitoxantrone. Values are mean±standard deviation from 2 independent experiments.

TABLE 8

Effect of FTA and FTB on S1-M1-3.2 cells.

| Drug (μM) | Per Cent Survival Alone | Per Cent Survival with 3.2 μM mitoxantrone | Difference Score |
|---|---|---|---|
| Fumitremorgin A | | | |
| 0.1 | 95 ± 1 | 96 ± 2 | −1 |
| 0.5 | 96 ± 2 | 95 ± 4 | 1 |
| 1 | 96 ± 1 | 94 ± 5 | 2 |
| 5 | 96 ± 1 | 64 ± 4 | 32 |
| 10 | 89 ± 9 | 40 ± 6 | 49 |
| 20 | 59 ± 4 | 35 ± 5 | 24 |
| 40 | 50 ± 8 | 34 ± 4 | 16 |
| 80 | 41 ± 8 | 34 ± 4 | 7 |
| Fumitremorgin B | | | |
| 0.1 | 94 ± 1 | 91 ± 5 | 3 |
| 0.5 | 95 ± 2 | 90 ± 3 | 5 |
| 1 | 93 ± 0 | 87 ± 1 | 6 |
| 5 | 90 ± 2 | 51 ± 4 | 39 |
| 10 | 91 ± 4 | 35 ± 1 | 56 |
| 20 | 59 ± 10 | 29 ± 1 | 30 |
| 40 | 41 ± 7 | 20 ± 2 | 21 |
| 80 | 16 ± 2 | 10 ± 1 | 6 |

Both FTA and FTB showed reduced activity in the reversal assay when compared to FTC (20- and 14-fold lower, respectively; as seen by comparing the data in Table 7 with Table 8) and were found to be more toxic than FTC (40% cell death at 20 μM compared with greater than 80 μM for FTC).

To determine the specificity of FTC for non P-gp multi-drug resistance, FTC was tested on S1-B1–20 cells which were selected for resistance to bisantrene and which express high levels of P-gp (Table 9)(Zhang, et al, Oncol. Res. 6291–301 (1994)). S1-B1–20 cells were grown in increasing doses of FTC or α-(3,4-dimethoxyphenyl)-3,4-dihydro-6,7-dimethoxy-α-[(4-methylphenyl)thio]-2(1H)-isoquinolineheptanenitrile, either alone or in combination with 21 μM bisantrene. The 21 μM concentration of bisantrene is not inhibitory to the growth of the cells. Values shown are mean ± standard deviation from triplicate test wells.

TABLE 9

Reversal of Resistance in P-gp Expressing Cells.

| Drug (μM) | Per Cent Survival Alone | Per Cent Survival with 21 μM bisantrene | Difference Score |
|---|---|---|---|
| Fumitremorgin C | | | |
| 0.1 | 99 ± 1 | 101 ± 1 | −4 |
| 0.5 | 99 ± 1 | 103 ± 1 | −4 |
| 1 | 98 ± 3 | 100 ± 0 | −2 |
| 5 | 101 ± 3 | 103 ± 2 | −2 |
| 10 | 88 ± 0 | 93 ± 1 | −4 |
| 20 | 85 ± 0 | 89 ± 1 | −4 |
| 40 | 83 ± 1 | 77 ± 2 | 13 |
| 80 | 35 ± 1 | 53 ± 5 | −18 |
| Alpha-(3,4-di-Methoxyphenyl)-3,4-dihydro-6,7-dimethoxy-alpha-[(4-methylphenyl)thio]-2(1H)-isoquinolineheptane nitrile | | | |
| 0.1 | 99 ± 4 | 92 ± 1 | 7 |
| 0.5 | 97 ± 1 | 10 ± 0 | 87 |
| 1 | 94 ± 2 | 4 ± 0 | 90 |
| 5 | 90 ± 1 | 4 ± 0 | 86 |
| 10 | 50 ± 1 | 4 ± 0 | 46 |
| 20 | 14 ± 1 | 4 ± 0 | 10 |
| 40 | 4 ± 0 | 4 ± 0 | 0 |
| 80 | 4 ± 0 | 4 ± 0 | 0 |

No resensitization to bisantrene (which is an excellent substrate for P-gp) was detected. However, resistance to bisantrene (Table 9) was reversible in S1-B1–20 cells by the P-gp reversal agent, α-(3,4-dimethoxyphenyl)-3,4-dihydro-6,7-dimethoxy-α-[(4-methylphenyl)thio]-2(1H)-isoquinolineheptanenitrile.

Reversal Activity of FTC

The reversal activity of FTC in S1-M1-3.2 cells was determined by using a fixed dose of FTC in combination with increasing doses of antitumor agent mitoxantrone, doxorubicin, paclitaxel, or topotecan (Table 10). Drug resistant S1-M1-3.2 or parental cells were cultured in the absence or presence of 5 μM FTC, along with increasing doses of chemotherapeutic agent mitoxantrone, doxorubicin, paclitaxel, or topotecan. Cell survival was estimated after 3 days using the SRB assay. Cell survival was determined by the SRB assay and $EC_{50}$ values were determined from toxicity curves. The dose modifying factor (DMF) is the ratio of $EC_{50}$ values obtained in the absence and presence of reversal agent. Maximum DMF values (shown in parentheses) is the ratio of $EC_{50}$ values of resistant and sensitive cells in the absence of the reversal agent. This value is obtained when resistance is reversed completely, and is the equivalent of the relative resistance.

TABLE 10

Activity of FTC in multiple cell lines

| | Dose modifying factor | | | |
|---|---|---|---|---|
| Cell line | Mitoxantrone | Doxorubicin | Paclitaxel | Topotecan |
| S1 | 1 | 1 | 1.4 | 0.9 |
| S1-M1 | 93 (1435) | 25.9 (54) | 1.1 (6) | 24 (41) |
| MCF 7 | 1.7 | 1.0 | 0.8 | |
| MCF 7/mtxR | 114 (2090) | 3.0 (11.4) | 1.1 (2.0) | |
| MCF 7 | 7.5 | 2.0 | 1.0 | |
| MCF 7/AdVp | 5000 (333,333) | 100 (2591) | 0.7 (10.7) | |
| HL-60 | 1.3 | 2.1 | 1.0 | |
| HL-60/AR | 3.3 (53) | 2.8 (92.3) | 2.6 (5.1) | |

As shown in Table 10, FTC (5 μM) significantly potentiated the toxicity of mitoxantrone (93-fold), doxorubicin (26-fold) and topotecan (24-fold). Reversal activity of FTC was not detected with paclitaxel in the resistant cells (1.1-fold) or with mitoxantrone, doxorubicin, paclitaxel, or topotecan in the parental S1 cells (1.0 to 1.4-fold).

In order to determine the utility of FTC as a reversal agent in other multidrug resistant cell lines, FTC was tested in two breast cancer cell lines which show a multidrug resistant phenotype with no overexpression of P-gp or MRP. In the human breast cell line MCF-7/mtx (a mitoxantrone-selected cell line), FTC reversed mitoxantrone resistance (114-fold) and doxorubicin resistance (3-fold) (Table 10). No reversal of paclitaxel resistance was found in these cells (1.1-fold) or in the parental unselected cells (0.8–1.7-fold). A second non P-gp, non MRP human breast cell line, MCF-7/AdrVp, was obtained by selection in doxorubicin, in the presence of the P-gp reversal agent verapamil [Chen et al., "Characterization of Adriamycin-Resistant Human Breast Cancer Cells Which Display Overexpression of a Novel Resistance-Related Membrane Protein," J. Biol. Chem., 265: 10073–10080, 1990]. Selection in doxorubicin and verapamil was done to favor the induction of non-P-gp forms of resistance. MCF-7/AdrVp cells were resistant to doxorubicin (2600-fold), but were profoundly more resistant to mitoxantrone (333,000-fold). FTC (5 μM) reversed resistance to both doxorubicin (100-fold) as well as mitoxantrone (5000-fold), with little effect on parental cells (Table 10). No reversal was seen to paclitaxel.

The activity of FTC was also examined on promyelocytic leukemia HL60/AR cells, which were selected for doxorubicin resistance, and express high levels of MRP message and proteins. FTC had no significant reversal activity in this cell line (2.6–3.3 fold) compared to the parental line, HL-60 (1.0–2.1 fold) even though significant resistance to mitoxantrone and doxorubicin was observed in the resistant line.

Effect of Fumitremorgin C on Drug Accumulation

To determine the mechanism of reversal activity by FTC, a drug accumulation analysis on drug sensitive and resistant cells using [$^{14}$C] mitoxantrone and [$^{14}$C] doxorubicin was performed. As shown in Table 2, addition of 1 μM FTC to the assay increased the amount of mitoxantrone (2-fold) and doxorubicin (3.4-fold) retained by the S1-M1-3.2 cells. The increase in mitoxantrone accumulation by FTC brought the level close to that seen in the parental cells. No effect was seen in the parental cells (S1) or in the P-gp expressing S1-B1–20 cells.

The mechanism by which FTC reverses drug resistance is unknown. FTC increases drug accumulation in drug resistant cells and while not wishing to be bound by theory, it is contemplated that FTC blocks the action of a putative drug transporter protein, and allows the cytotoxic agent to reach lethal levels within the resistant cell. FTC, mitoxantrone, and doxorubicin are multi-ring, planar molecules, and therefore, FTC may compete with these molecules for the binding site on the transporter. Consistent with this hypothesis, cells selected in mitoxantrone are cross-resistant to topotecan, another planar aromatic anticancer drug, and FTC reverses resistance to this agent. An interesting feature of this putative transporter is the narrow structural range of transported substrates, compared to P-gp and MRP. The transporter appears to mediate resistance primarily to mitoxantrone, with much lower levels of resistance to the related anthracyclines, doxorubicin and bisantrene. This preference for mitoxantrone is observed even in cell lines selected for drug resistance in doxorubicin (MCF 7/AdVp, see Table 10). Consistent with this substrate selectivity, MCF/MX cells are only 3.2-fold resistant to camptothecin but 120-fold resistant to the closely related analogue, 9-amino camptothecin. Finally, FTC was superior to FTA and FTB, in reversal assays.

Effect of FTC on Cells Transfected with a Gene that Mediates Mitoxantrone Resistance The gene encoding a mitoxantrone transporter protein has recently been cloned (Doyle, et al. "A Multidrug Resistance Transporter from Human MCF-7 Breast Cancer Cells", Proc. Natl. Acad. Sci. USA 95, 15665–15670, 1998; Allikmets et al. "A Human Placenta-specific ATP-Binding Cassette Gene (ABCP) on Chromosome 4q22 That Is Involved in Multidrug Resistance" Cancer Res. 58, 5337–5339, 1998; Miyake et al. "Molecular Cloning of cDNAs Which Are Highly Overexpressed in Mitoxantrone-resistant Cells: Demonstration of Homology to ABC Transport Genes Cancer Res. 59, 8–13, 1999). Introduction of the gene for this transporter, variously termed breast cancer resistance protein (BCRP), mitoxantrone resistance gene (MXR) or placenta-specific ABC transporter (ABCP) into MCF-7 breast cancer cells (MCF-7/BCRP) confers resistance to mitoxantrone, daunorubicin and doxorubicin, but not to cisplatin, vincristine, and paclitaxel. The phenotype of the transfected cells is similar to that of the mitoxantrone-selected S1-M1-3.2 cell line which was used to identify FTC. The BCRP/MXR/ABCP gene is also overexpressed in S1-M1-3.2 cells compared to the S1 parental cells (Ross et al. "Atypical Multidrug Resistance: Breast Cancer Resistance Protein Messenger RNA Expression in Mitoxantrone-Selected Cell Lines" J. Natl Cancer Inst. 91:429–433, 1999). Multidrug resistance mediated by BCRP/MXR/ABCP and determination of whether reversible by FTC is shown in Table 11.

The reversal activity of FTC in BCRP-transfected cells was determined by using a fixed dose of FTC in combination with increasing doses of antitumor drugs Mitoxantrone, Doxorubicin, Topotecan and Paclitaxel. Cell survival was estimated after 3 days using the SRB assay, and $EC_{50}$ values were determined from cytotoxicity curves. Dose modifying factors (DMF) are shown in Table 11, with maximum DMF values in parentheses.

TABLE 11

Activity of FTC in BCRP-transfected cells

| | Dose modifying factor (5 μM FTC) | | | |
|---|---|---|---|---|
| Cell line | Mitoxantrone | Doxorubicin | Topotecan | Paclitaxel |
| MCF-7 | 2.5 | 1.0 | 5.6 | 0.7 |
| MCF-7/BCRP | 29.4 (35.1) | 6.6 (7.6) | 6.5 (3.3) | 1.1 (2.7) |

FTC (5 μM) potentiated the toxicity of mitoxantrone (29.4-fold), doxorubicin (6.6-fold) and topotecan (6.5-fold). No reversal activity was detected with paclitaxel (1.1-fold). Some reversal by FTC was also detected in the untransfected MCF-7 cells with mitoxantrone and topotecan (2.5–5.6 fold). This is postulated to be due to a low level of expression of BCRP in these cells, and suggests that intrinsic resistance to mitoxantrone may occur in some cell lines in the absence of drug selection.

To investigate the mechanism of reversal activity, MCF-7 and MCF-7/BCRP cells were exposed to 1 μM daunorubicin or 1 μM [$^{14}$C]-doxorubicin for 1.5–2 hours (accumulation phase), washed, and incubated in the absence of the antitumor agent for 1 hour (retention phase). All incubations were carried out in the absence or presence of FTC (1 or 5 μM). The amount of antitumor drug remaining in the cells at the end of the retention phase was quantified by fluorescence analysis (daunorubicin) or by scintillation counting (doxorubicin). Values shown represent the mean of duplicate (daunorubicin) or triplicate (doxorubicin) determinations±standard deviation.

TABLE 12

Effect of FTC on daunorubicin retention in BCRP-transfected cells.

| | Channel Number (fluorescence units) | | |
|---|---|---|---|
| Cell line | No FTC | 1 μM FTC | 5 μM FTC |
| MCF-7 | 15.2 ± 0.39 | 16.0 ± 0.98 | 16.8 ± 1.0 |
| MCF-7/BCRP | 6.8 ± 0.33 | 12.2 ± 1.78 | 15.6 ± 0.94 |

TABLE 13

Effect of FTC on [$^{14}$C] doxorubicin retention in BCRP-transfected cells.

| | DPM per microgram protein | | |
|---|---|---|---|
| Cell line | No FTC | 1 μM FTC | 5 μM FTC |
| MCF-7 | 10.4 ± 1.24 | 10.3 ± 0.26 | 11.0 ± 0.71 |
| MCF-7/BCRP | 5.4 ± 0.48 | 9.5 ± 0.63 | 9.9 ± 0.18 |

As shown in Tables 12 and 13, FTC treatment increased the amount of daunorubicin (1.8–2.3 fold) and [$^{14}$C]-doxorubicin (1.8-fold) retained by MCF-7/BCRP cells, compared with untreated cells. The increase in drug retention by FTC brought the level close to that seen in the untransfected cells. No effect of FTC was observed in the untransfected MCF-7 cells. These data show that FTC reverses resistance mediated by the BCRP gene product. However, FTC may also reverse resistance mediated by genes other than BCRP.

The $IC_{50}$'s of diketopiperazines of Formula (I) in resensitizing the S1-M1-3.2 human colon cancer cells to mitoxantrone (50% cancer cell death) and the toxicity (concentration that causes greater than 20% cell death) of the diketopiperazines of Formula (I) alone against the S1-M1-3.2 cells are presented in Table 14.

TABLE 14

Resensitizing the S1-M1-3.2 Human Colon Cancer Cells to Mitoxantrone and Toxicity of Fumitremorgin A, B and C and Diketopiperazines Against S1-M1-3.2

| Example No. | IC50 ($\mu$M) | Toxicity (>20%) ($\mu$M) |
| --- | --- | --- |
| Fumitremorgin A | 7.0 | 15.0 |
| Fumitremorgin B | 5.0 | 15.0 |
| Fumitremorgin C | 0.3 | >80.0 |
| 14a | 80.0 | 80.0 |
| 14b | 1.0 | 35.0 |
| 15a | 35.0 | >80.0 |
| 15b | 15.0 | >80.0 |
| 16a | >80.0 | >80.0 |
| 16b | 5.5 | >80.0 |
| 17a | 35.0 | 50.0 |
| 17b | 3.5 | >80.0 |
| 18a | 50.0 | 15.0 |
| 18b | 1.5 | 25.0 |
| 19a | 11.0 | 50.0 |
| 19b | 4.0 | >80.0 |
| 20a | 30.0 | 80.0 |
| 20b | 2.0 | 50.0 |
| 21a | 10.5 | 10.0 |
| 21b | 6.0 | >80.0 |
| 22a | 15.0 | 80.0 |
| 22b | 2.5 | >80.0 |
| 23a | 0.3 | 7.5 |
| 23b | 3.0 | >80 |
| 24a | 10 | 50 |
| 24b | 2.0 | 20 |
| 25 | 15 | >80 |
| 26 | 7.0 | >80.0 |
| 27 | 2.5 | >80 |
| 28 | 0.25 | 7.0 |
| 29a | 20 | >80 |
| 29b | >80 | >80 |
| 30 | >80 | >80 |
| 31 | 65 | >80 |
| 32 | >80 | >80 |
| 33 | >80 | >80 |
| 34 | 1.0 | 2.0 |

Fumitremorgin A, B and C and compounds of Formula (I) can be administered either separately or in admixture with chemotherapeutic agents and, if administered separately, can be administered either prior to, concurrently, or after administration of the chemotherapeutic agent to which the cancer cells have expressed resistance. Fumitremorgin A, B and C and compounds of Formula (I) can be administered orally, parenterally or intravaneously or as a solid dosage form, i.e., tablet, capsule, lozenge or suppository.

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

All formulations shall contain an amount of Fumitremorgin A, B and C or a compound of Formula (I) which effectively reverses the drug resistance of the target cells and may additionally be combined with a therapeutically effective amount of the anticancer drug being used in conjunction with Fumitremorgin A, B and C or a compound of Formula (I) to overcome the multiple drug resistance. Precise dosages for oral, parenteral, or intravenous administration will be determined by the administering physician based on experience with the individual subject treated and standard medical principles.

This new Fumitremorgin A, B and C producing strain of *Aspergillus fumigatus* was isolated from a desert soil sample collected in Chihuahuan, Mexico and is maintained in the culture collection of Wyeth-Ayerst, Lederle Laboratories, American Cyanamid Company, American Home Products Corporation, Pearl River, N.Y. 10965 as culture number LL-S266. A viable culture of this new producing strain was deposited with the Culture Collection Laboratory, Northern Utilization Research and Development Division, U.S. Department of Agriculture, Peoria, Ill. on Jun. 7, 1999 and added to its permanent collection under accession number NRRLL-30140 in accordance with the Budapest Treaty and is freely available to the public from this depository.

The compounds of this invention and their preparation can be understood further by the following examples, but should not constitute a limitation thereof.

Preparation of Fumitremorgin A, Fumitremorgin B and Fumitremorgin C by Fermentation The culture of *Aspergillus fumigatus* was stored frozen at −140° C. in Potato Dextrose Broth (FM-3) with 25% glycerol. The culture was revived by streaking a Bennett's Agar plate and incubating at 22° C. for 7–10 days. Seed-1 was prepared by inoculating 2–3 loops full of the culture from the plate into a tube containing 10 ml of FM-3 and incubating at 22° C. and 150 rpm for 4 days. Seed-2 was prepared by transferring seed-1 into a 250 ml Erlenmeyer flask containing 50 ml FM-3 and incubating for an additional 4 days at 22° C. and 200 rpm. Seed-2 was homogenized by gentle grinding and 2.5 ml volume was inoculated into the fermentation medium FM-5 (15 g white rice+5 ml 0.1% yeast extract in a 250 ml Erlenmeyer flask). After 7–10 days of stationary fermentation at 22° C., the content of the flask was extracted with 30 ml methanol. The methanolic extract was purified by column chromatography on an LH-20 column with MeOH as solvent, followed by HPLC separation on a $C_{18}$ column (ODS-A,10 micron, 40×250 mm). The mobile phase was a gradient solvent system with increasing MeOH in water to afford fumitremorgin C (FTC), fumitremorgin B (FTB) and fumitremorgin A (FTA). FTC was crystallized from methanol or ethyl acetate and the purity was estimated to be 90–95%, based on high performance liquid chromatography analysis. Structures were determined by spectroscopic methods. Fractions at each stage of the purification were screened for reversal activity using a drug accumulation assay.

EXAMPLE 1

(3S)-1H-Pyrido[3,4-b]indole-3-carboxylic acid, 2,3, 4,9-tetrahydro-1-(2-methylpropyl)-methyl ester To the suspension of L-tryptophan methyl ester hydrochloride (1 mmol) in dry toluene(150 ml), was added isovaleraldehyde (1 mmol). The resulting mixture was refluxed for about 15 hours with stirring and cooled to room temperature before methanol (100 ml) was added to dissolve the products. The organic solution, upon filtration, was concentrated in vacuo to afford the hydrochloride salts of a pair of diastereoisomers at C-1 of the desired product with quantitative yield and a 2:1 cis/trans ratio.

EXAMPLE 2

(3S)-1H-Pyrido[3,4-b]indole-3-carboxylic acid, 2,3, 4,9-tetrahydro-1-(2-Methyl-1-propenyl)-methyl ester The compound was prepared by procedures described for example 1, except that isovaleraldehyde was replaced with 3-methyl-2-butenal.

EXAMPLE 3

(3S)-1H-Pyrido[3,4-b]indole-3-carboxylic acid, 2,3, 4,9-tetrahydro-1-nonyl-methyl ester The compound was prepared by procedures described for example 1, except that isovaleraldehyde was replaced with decyl aldehyde.

EXAMPLE 4

(3S)-1H-Pyrido[3,4-b]indole-3-carboxylic acid, 2,3, 4,9-tetrahydro-1-(5-phenylpentyl)-methyl ester The compound was prepared by procedures described for example 1, except that isovaleraldehyde was replaced with 6-phenyldecanal.

EXAMPLE 5

(3S)-1H-Pyrido[3,4-b]indole-3-carboxylic acid, 2,3, 4,9-tetrahydro-1-(3-benzyloxycarbamate-propyl)-methyl ester A mixture of L-tryptophan methyl ester hydrochloride (2.0 mmol), p-toluenesulfonic acid (0.5 mmol), and 4-benzyloxycarbamate-butyraldehyde diethyl acetal (2.0 mmol), in N,N-dimethylformamide (2 mL) was stirred at 110° C. for 45 min. The yellowish solution was cooled to room temperature, before sodium bicarbonate solution (sat., 100 mL) was added. The products were extracted with ethyl acetate (200 mL), washed with water, dried, and evaporated in vacuo to afford the hydrochloride salts of a pair of diastereoisomers at C-1 with quantitative yield. The 4-benzyloxycarbamate-butyraldehyde diethyl acetal was synthesized by reacting 4-animo-butyraldehyde diethyl acetal with benzyloxycarbonyl chloride in sodium carbonate solution (sat.) at room temperature.

EXAMPLE 6

(3S)-1H-Pyrido[3,4-b]indole-3-carboxylic acid, 2,3, 4,9-tetrahydro-methyl ester

A solution of L-tryptophan methyl ester hydrochloride (2.1 mmol), p-toluenesulfonic acid (0.5 mmol) in 1:1 N,N-dimethylformamide/diethoxymethane (4 ml total) was refluxed for 30 minutes. The reaction mixture was partitioned between ethyl acetate (200 ml) and 10% sodium bicarbonate (200 ml). The organic layer was separated, washed with water and evaporated in vacuo to afford the desired product with quantitative yield.

EXAMPLE 7

(3S)-1H-Pyrido[3,4-b]indole-3-carboxylic acid, 2,3, 4,9-tetrahydro-1-methyl-methyl ester The compound was prepared by procedures described for example 6, except that the diethoxymethane was replaced with acetaldehyde diethyl acetal.

EXAMPLE 8

(3R)-1H-Pyrido[3,4-b]indole-3-carboxylic acid, 2,3, 4,9-tetrahydro-1-(2-methylpropyl)-methyl ester The compound was prepared by procedures described for example 1, except that the L-tryptophan methyl ester hydrochloride was replaced with its D enantiomer.

EXAMPLE 9

2,2,2-Trichloroethoxy-carbonyl(Troc)-L-prolyl Chloride

Solutions of 2,2,2-trichloroethyl chloroformate (2.0 mmol) in ether (1 ml), and 2N sodium hydroxide (1 ml) were carefully added simultaneously to a vigorously stirred emulsion of L-proline (1.6 mmol) in 2N NaOH (1 ml) and ether (0.5 ml) with ice-cooling. The bath was removed and the reaction mixture was stirred for one hour. The aqueous layer, washed with ether, was acidified with concentrate hydrochloric acid to pH 1. The product was extracted with ether, washed with water, dried over sodium sulfate, and evaporated under reduced pressure to afford 2,2,2-trichloroethoxy-carbonyl(Troc)-proline as a colorless oil with quantitative yield. The 2,2,2-trichloroethoxy-carbonyl(Troc)-proline (1 mmol) was dissolved in thionyl chloride (1.5 mmol) and the solution stirred for 15 hours at ambient temperature. The volatiles were removed by evaporation under reduced pressure to obtain a colorless oil, identified as the desired product by NMR analysis.

EXAMPLE 10

Troc-S-(–)-2-Azetidinecarboxyl Chloride

The product of the example was prepared using the procedure of Example 9 with the exception that L-proline was replaced by S-(–)-2-Azetidinecarboxylic acid.

EXAMPLE 11

Troc-L-pipecolinyl Chloride

The product of the example was prepared using the procedure of Example 9 with the exception that L-proline was replaced with L-pipecolinic acid.

EXAMPLE 12

Troc-D-prolinyl Chloride

The product of the example was prepared using the procedure of Example 9 with the exception that L-proline was replaced with D-proline.

EXAMPLE 13

Troc-D-pipecolinyl Chloride

The product of the example was prepared using the procedure of Example 9 with the exception that L-proline was replaced with D-pipecolinic acid.

EXAMPLES 14a AND 14b (5aS,12R,14aS)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(14a) and
(5aS,12S,14aS)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(14b)

To the stirred solution of (3S)-1H-Pyrido[3,4-b]indole-3-carboxylic acid, 2,3,4,9-tetrahydro-1-(2-methylpropyl)-methyl ester (1.0 mmol) in dry dichloromethane (5.0 ml) and triethylamine (0.3 g), was slowly added Troc-L-prolyl chloride at 1:1 molar ratio in dichloromethane (2.0 ml) with ice-cooling. The bath was removed and the reaction mixture was stirred at ambient temperature for 1 hour before diluted with dichloromethane (50 ml). The organic solution was then washed sequentially with water, sodium bicarbonate (sat.) and water, dried over sodium sulfate, and evaporated to afford a yellowish powder.

The powder was then dissolved in 2:1 methanol/dichloromethane (2.0 ml) and refluxed in the presence of zinc dust (0.3 g) for 2 hours. The metal was removed by filtration through diatomaceous earth and the organic solution evaporated to afford a yellowish solid, which was suspended in 5% hydrochloric acid (100 ml) and extracted by dichloromethane (2×50 ml). The combined organic layer was washed with water, dried and evaporated in vacuo to yield a mixture of diastereoisomer pair with 2:3 12R/12S ratio.

The mixture was further separated by HPLC on a C18 column using mobile phase that consisted of gradient solvent system of acetonitrile in water to afford desired products in pure form with a 54% overall combined yield. ESIMS (MH$^+$): 14a, 352.1; 14b, 352.2.

EXAMPLES 15a AND 15b (5aR,12R,14aS)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(15a) and
(5aR,12S,14aS)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(15b)

The compounds were prepared by procedures described for Examples 14a and 14b, except that the (3S)-1H-Pyrido[3,4-b]indole-3-carboxylic acid, 2,3,4,9-tetrahydro-1-(2-methylpropyl)-methyl ester was replaced by (3R)-1H-Pyrido[3,4-b]indole-3-carboxylic acid, 2,3,4,9-tetrahydro-1-(2-methylpropyl)-methyl ester. ESIMS(MH$^+$): 15a, 352.2; 15b, 352.2.

EXAMPLES 16a AND 16b (5aS,12R,14aR)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(16a) and
(5aS,12S,14aR)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(16b)

The compounds were prepared by procedures described for Examples 14a and 14b, except that the Troc-L-prolyl chloride was replaced with Troc-D-prolyl chloride. ESIMS (MH$^+$): 16a, 352.2; 16b, 352.2.

EXAMPLES 17a AND 17b (5aR,12R,14aR)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(17a) and
(5aR,12S,14aR)-12-isobutyl-1,2,3,5a,6,11,12,14a-octahydro-5H,14H-pyrrolo[1″,2″:4′,5′]pyrazino[2′,1′:6,1]pyrido[3,4-b]indole-5,14-dione(17b)

The compounds were prepared by procedures described for Examples 14a and 14b, except that the (3S)-1H-Pyrido[3,4-b]indole-3-carboxylic acid, 2,3,4,9-tetrahydro-1-(2-methylpropyl)-methyl ester and Troc-L-prolyl chloride were respectively replaced with (3R)-1H-Pyrido[3,4-b]indole-3-caboxylic acid, 2,3,4,9-tetrahydro-1-(2-methylpropyl)-methyl ester and Troc-D-prolyl chloride. ESIMS(MH$^+$): 17a, 352.3; 17b, 352.2.

EXAMPLES 18a AND 18b (6aS,13R,15aS)-13-isobutyl-1,2,3,4,6a,7,12,13,15a-nonahydro-6H,15H-pyrido[1″,2″:4′,5′]pyrazino[2′,1′:6,1]pyrido[3,4-b]indole-6H,15H-dione(18a) and
(6aS,13S,15aS)-13-isobutyl-1,2,3,4,6a,7,12,13,15a-nonahydro-6H,15H-pyrido[1″,2″:4′,5′]pyrazino[2′,1′:6,1]pyrido[3,4-b]indole-6H,15H-dione(18b)

The compounds were prepared by procedures described for Examples 14a and 14b, except that the Troc-L-prolyl chloride was replaced with Troc-L-pipecolinyl chloride. ESIMS (MH$^+$): 18a, 366.2; 18b, 366.2.

EXAMPLES 19a AND 19b (6aR,13R,15aS)-13-isobutyl-1,2,3,4,6a,7,12,13,15a-nonahydro-6H,15H-pyrido[1″,2″:4′,5′]pyrazino[2′,1′:6,1]pyrido[3,4-b]indole-6H,15H-dione(19a) and
(6aR,13S,15aS-13-isobutyl-1,2,3,4,6a,7,12,13,15a-nonahydro-6H,15H-pyrido[1″,2″:4′,5′]pyrazino[2′,1′:6,1]pyrido[3,4-b]indole-6H,15H-dione(19b)

The compounds were prepared by procedures described for Examples 15a and 15b, except that the Troc-L-prolyl chloride was replaced with Troc-L-pipecolinyl chloride. ESIMS (MH$^+$): 19a, 366.1; 19b, 366.3.

EXAMPLES 20a AND 20b (6aS,13R,15aR)-13-isobutyl-1,2,3,4,6a,7,12,13,15a-nonahydro-6H,15H-pyrido[1″,2″:4′,5′]pyrazino[2′,1′:6,1]pyrido[3,4-b]indole-6H,15H-dione(20a) and
(6aS,13S,15aR)-13-isobutyl-1,2,3,4,6a,7,12,13,15a-nonahydro-6H,15H-pyrido[1″,2″:4′,5′]pyrazino[2′,1′:6,1]pyrido[3,4-b]indole-6H,15H-dione(20b)

The compounds were prepared by procedures described for Examples 16a and 16b, except that the Troc-D-prolyl chloride was replaced with Troc-D-pipecolinyl chloride. ESIMS (MH+): 20a, 366.2; 20b, 366.2.

EXAMPLES 21a AND 21b (6aR,13R,15aR)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione(21a) and (6aR,13S,15aR)-13-isobutyl-1,2,3,4,6a,7,12,13,15a-nonahydro-6H,15H-pyrido[1",2":4',5']pyrazino[2',1':6,1]pyrido[3,4-b]indole-6H,15H-dione(21b)

The compounds were prepared by procedures described for Examples 17a and 17b, except that the Troc-D-prolyl chloride was replaced with Troc-D-pipecolinyl chloride. ESIMS (MH+): 21a, 366.1; 21b, 366.2.

EXAMPLES 22a AND 22b (4aS,11R,13aS)-11-isobutyl-1,4a,5,10,11,13a-hexahydro-4H-azeto[1",2":4',5']pyrazino[2',1':6,1]pyrido[3,4-b]indole-4,13(2H)-dione(22a) and (4aS,11S,13aS)-11-isobutyl-1,4a,5,10,11,13a-hexahydro-4H-azeto[1",2":4',5']pyrazino[2',1':6,1]pyrido[3,4-b]indole-4,13(2H)-dione(22b)

The compounds were prepared by procedures described for Examples 14a and 14b, except that the Troc-L-prolyl chloride was replaced with S-(–)-2-Azetidinecarboxyl chloride. ESIMS(MH+): 22a, 338.2; 22b, 338.1.

EXAMPLES 23a AND 23b (5aS,12R,14aS)-12-(5-phenylpentyl)-1,2,3,5a,6,11,12,14a-octahydro-5H,14H-pyrrolo[1",2":4',5']pyrazino[2',1':6,1]pyrido[3,4-b]indole-5,14-dione (23a) and (5aS,12S,14aS)-12-(5-phenylpentyl)-1,2,3,5a,6,11,12,14a-octahydro-5H,14H-pyrrolo[1",2":4',5']pyrazino[2',1':6,1]pyrido[3,4-b]indole-5,14-dione(23b)

As described for examples 14a and 14b, but substituting (3S)-1H-Pyrido[3,4-b]indole-3-carboxylic acid, 2,3,4,9-tetrahydro-1-(5-phenylpentyl)-methyl ester for (3S)-1H-Pyrido[3,4-b]indole-3-carboxylic acid, 2,3,4,9-tetrahydro-1-(2-methylpropyl)-methyl ester), the desired compounds were prepared. ESIMS (MH+): 23a, 442.2; 23b, 442.2.

EXAMPLES 24a AND 24b

Benzyl 3-[(5aS,12R,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propylcarbamate(24a) and Benzyl 3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propylcarbamate(24b)

(ESIMS, MH+) (24a, 487.1) (24b, 487.2).

As described for examples 14a and 14b, but substituting (3S)-1H-Pyrido[3,4-b]indole-3-carboxylic acid, 2,3,4,9-tetrahydro-1-(3-benzyloxycarbamate-propyl)-methyl ester for (3S)-1H-Pyrido[3,4-b]indole-3-carboxylic acid, 2,3,4,9-tetrahydro-1-(2-methylpropyl)-methyl ester), the desired compounds were prepared. ESIMS (MH+): 24a, 487.1; 24b, 487.2.

EXAMPLE 25

(5aS,14aS)-1,2,3,5a,6,11,12,14a-octahydro-5H,14H-pyrrolo[1",2":4',5']pyrazino[2',1':6,1]pyrido[3,4-b]indole-5,14-dione As described for examples 14a and 14b, but substituting (3S)-1H-Pyrido[3,4-b]indole-3-carboxylic acid, 2,3,4,9-tetrahydro-methyl ester for (3S)-1H-Pyrido[3,4-b]indole-3-carboxylic acid, 2,3,4,9-tetrahydro-1-(2-methylpropyl)-methyl ester), the desired compound was prepared. ESIMS (MH+): 296.3.

EXAMPLE 26

(5aS,12S,14aS)-12-methyl-1,2,3,5a,6,11,12,14a-octahydro-5H,14H-pyrrolo[1",2":4',5']pyrazino[2',1':6,1]pyrido[3,4-b]indole-5,14-dione As described for examples 14a and 14b, but substituting (3S)-1H-Pyrido[3,4-b]indole-3-carboxylic acid, 2,3,4,9-tetrahydro-1-methyl-methyl ester for (3S)-1H-Pyrido[3,4-b]indole-3-carboxylic acid, 2,3,4,9-tetrahydro-1-(2-methylpropyl)-methyl ester), the desired compound was prepared. 12S isomer was the predominant product, and was the only one isolated. ESIMS (MH+): 310.3.

EXAMPLE 27

(5aS,12S,14aS)-12-(2-methylprop-1-enyl)-1,2,3,5a,6,11,12,14a-octahydro-5H,14H-pyrrolo[1",2":4',5']pyrazino[2',1':6,1]pyrido[3,4-b]indole-5,14-dione As described for example 14, but substituting (3S)-1H-Pyrido[3,4-b]indole-3-carboxylic acid, 2,3,4,9-tetrahydro-1-(2-methyl-1-propenyl)-methyl ester for (3S)-1H-Pyrido[3,4-b]indole-3-carboxylic acid, 2,3,4,9-tetrahydro-1-(2-methylpropyl)-methyl ester), the desired compound was prepared. 12S isomer was the predominant product, and was the only one isolated. ESIMS (MH+): 350.2.

EXAMPLE 28

(5aS,12S,14aS)-12-nonyl-1,2,3,5a,6,11,12,14a-octahydro-5H,14H-pyrrolo[1",2":4',5']pyrazino[2',1':6,1]pyrido[3,4-b]Indole-5,14-dione As described for examples 14a and 14b, but substituting (3S)-1H-Pyrido[3,4-b]indole-3-carboxylic acid, 2,3,4,9-tetrahydro-1-nonyl-methyl ester for (3S)-1H-Pyrido[3,4-b]indole-3-carboxylic acid, 2,3,4,9-tetrahydro-1-(2-methylpropyl)-methyl ester), the desired compound was prepared. 12S isomer was the predominant product, and was the only one isolated. ESIMS (MH+): 422.2.

EXAMPLES 29a AND 29b (5aS,12R,14aS)-12-(3-aminopropyl)-1,2,3,5a,6,11,12,14a-octahydro-5H,14H-pyrrolo[1",2":4',5']pyrazino[2',1':6,1]pyrido[3,4-b]indole-5,14-dione (29a) and (5aS,12S,14aS)-12-(3-aminopropyl)-1,2,3,5a,6,11,12,14a-octahydro-5H,14H-pyrrolo[1",2":4',5']pyrazino[2',1':6,1]pyrido[3,4-b]indole-5,14-dione (29b)

The solution of benzyl 3-[(5aS,12R,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propylcarbamate (0.1 mmol) in methanol (2.0 ml) was stirred under hydrogen (1.5 atm) in the presence of 5% Palladium on carbon for 1 hour. The solid was removed by filtration, and the solution was evaporated to afford (5aS,12R,14aS)-12-(3-aminopropyl)-1,2,3,5a,6,11,12,14a-octahydro-5H,14H-pyrrolo[1",2":4',5']pyrazino[2',1':6,1]pyrido[3,4-b]indole-5,14-dione (95%). The (5aS,12S,14aS)-12-(3-aminopropyl)-1,2,3,5a,6,11,12,14a-octahydro-5H,14H-pyrrolo[1",2":4',5']pyrazino[2',1':6,1]pyrido[3,4-b]indole-5,14-dione was prepared in a similar manner, but using 3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propylcarbamate as starting material. ESIMS (MH+): 29a, 353.2; 29b, 353.2.

EXAMPLE 30

N-{3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propyl}Acetamide To a solution of (5aS,12S,14aS)-12-(3-aminopropyl)-1,2,3,5a,6,11,12,14a-octahydro-5H,14H-pyrrolo[1",2":4',5']pyrazino[2',1':6,1]pyrido[3,4-b]indole-5,14-dione (25 mg) in pyridine (0.5 ml) was added 3 drops of acetic anhydride, and the reaction mixture was stirred for 15 hours. The solution was evaporated and the residue purified by HPLC using a C18 column and gradient solvent of acetonitrile in water to afford the desired product (26 mg). ESIMS (MH+): 395.1.

EXAMPLE 31

N-{3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propyl}Butanamide As described for Example 30, but substituting butyric anhydride for acetic anhydride the product of the example was prepared. ESIMS (MH+): 423.2.

EXAMPLE 32

4-({3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propyl}amino)-4-oxobutanoic acid As described for Example 30, but substituting succinic anhydride for acetic anhydride the product of the example was prepared. ESIMS (MH+): 453.2.

EXAMPLE 33

(2S)-N-{3-[(5aS,12S,14aS)-5,14-dioxo-2,3,5a,6,11,12,14,14a-octahydro-1H,5H-pyrrolo[1",2":4',5']pyrazino[2',1':6,1]pyrido[3,4-b]indol-12-yl]propyl}pyrrolidine-2-carboxamide The compound was prepared by using procedure described for Example 30, but replacing acetic anhydride with Troc-L-prolyl chloride. The Troc group was then removed by refluxing with zinc dust and the product was purified by HPLC. ESIMS (MH+) 450.3.

EXAMPLE 34

(5aS,12S,14aS)-9-methoxy-11-(3-methylbut-2-enyl)-12-(2-methylprop-1-enyl)-1,2,3,5a,6,11,12,14a-octahydro-5H,14H-pyrrolo[1",2":4',5']pyrazino[2',1':6,1]pyrido[3,4-b]indole-5,14-dione To a stirred suspension of sodium hydride (0.12 mol) in dry dichloromethane (0.1 ml) was added a solution of fumitremorgin C (0.05 mmol) in dichloromethane (0.5 ml) under an atmosphere of nitrogen at room temperature. Upon stirring for forty-five minutes, 3,3-dimethyl allyl bromide (0.11 mmol) was added and the reaction mixture stirred under nitrogen for two hours. Saturated aqueous solution of ammonium chloride was then added, and the alkylation product was extracted with ethyl acetate and purified by HPLC on a C18 column using methanol/water as mobile phase. MS and $^1$H NMR spectra were consistent with the desired product.

We claim:

1. A method for resensitizing S1-M1-3.2 multiple drug resistant cancer cells to treatment with a chemotherapeutic agent to which said cancer cells have developed resistance comprising administration of an effective amount of a chemosensitizing reversal agent selected from compounds of Formula (I)

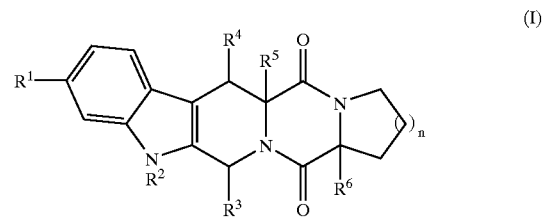

wherein:

n is an integer of 0, 1, or 2;

$R^1$ is hydrogen or alkoxy of 1 to 10 carbon atoms;

$R^2$ is hydrogen or alkenyl of 2 to 10 carbon atoms;

$R^3$ is hydrogen, alkyl of 1 to 10 carbon atoms, alkenyl of 2 to 10 carbon atoms, $R^7NH(CH_2)v$- or

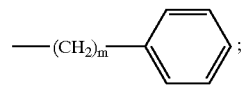

m is an integer of 1 to 6;

v is an integer of 1 to 4;

$R^4$, $R^5$ and $R^6$ are hydrogen;

$R^7$ is H or

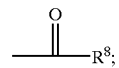

$R^8$ is selected from alkyl of 1 to 10 carbon atoms, —$(CH_2)_mCO_2H$,

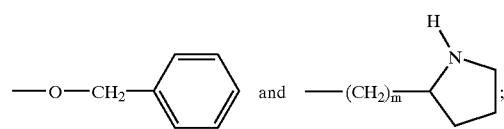

or a pharmaceutically acceptable salt thereof, Fumitremorgin A, Fumitremorgin B and Fumitremorgin C and a chemotherapeutic agent resistant to said cancer cells.

2. The method according to claim 1 wherein the chemotherapeutic agent is selected from the group consisting of mitoxantrone, doxorubicin and topotecan.

3. The method of claim 1 wherein the chemosensitizing reversal agent is administered prior to, concurrently with, or after administration of the chemotherapeutic agent.

4. A method for resensitizing BCRP-mediated multiple drug resistant cancer cells S1-M1-3.2 to treatment with a chemotherapeutic agent to which said cancer cells have developed resistance comprising administration of an effective amount of a chemosensitizing reversal agent selected from compounds of Formula (I)

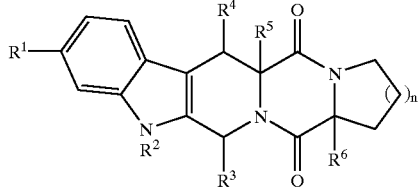

wherein:

n is an integer of 0, 1, or 2;

$R^1$ is hydrogen or alkoxy of 1 to 10 carbon atoms;

$R^2$ is hydrogen or alkenyl of 2 to 10 carbon atoms;

$R^3$ is hydrogen, alkyl of 1 to 10 carbon atoms, alkenyl of 2 to 10 carbon atoms, $R^7NH(CH2)v$- or

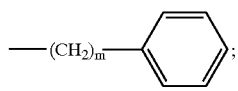

m is an integer of 1 to 6;

v is an integer of 1 to 4;

$R^4$, $R^5$ and $R^6$ are hydrogen;

$R^7$ is H or

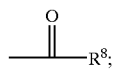

$R^8$ is selected from alkyl of 1 to 10 carbon atoms, $-(CH_2)_mCO_2H$,

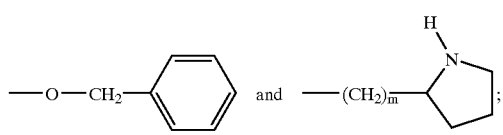

or a pharmaceutically acceptable salt thereof, Fumitremorgin A, Fumitremorgin B and Fumitremorgin C and a chemotherapeutic agent resistant to said cancer cells.

5. The method according to claim 4 wherein the chemotherapeutic agent is selected from the group consisting of mitoxantrone, doxorubicin, and topotecan.

6. The method according to claim 4 wherein the chemosensitizing reversal agent is administered prior to, concurrently with, or after administration of the chemotherapeutic agent.

7. A method of reversing BCRP or other non P-gp/non MRP mediated resistance of cancer cells to chemotherapeutic agents in a mammal which comprises administration of an effective amount of a chemosensitizing reversal agent selected from compounds of Formula (I)

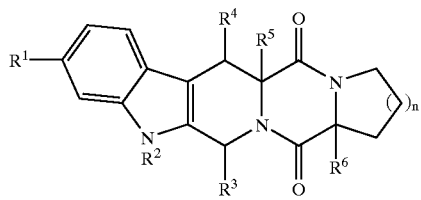

wherein:

n is an integer of 0, 1, or 2;

$R^1$ is hydrogen or alkoxy of 1 to 10 carbon atoms;

$R^2$ is hydrogen or alkenyl of 2 to 10 carbon atoms;

$R^3$ is hydrogen, alkyl of 1 to 10 carbon atoms, alkenyl of 2 to 10 carbon atoms, $R^7NH(CH2)v$- or

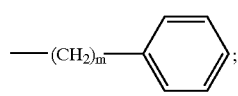

m is an integer of 1 to 6;

v is an integer of 1 to 4

$R^4$, $R^5$ and $R^6$ are hydrogen;

$R^7$ is H or

$R^8$ is selected from alkyl of 1 to 10 carbon atoms, $-(CH_2)_mCO_2H$,

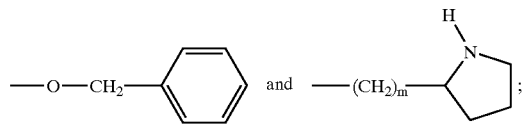

or a pharmaceutically acceptable salt thereof, Fumitremorgin A, Fumitremorgin B and Fumitremorgin C to said mammal in need thereof having a BCRP or other non-P-gp/non MRP mediated resistant cancer and a chemotherapeutic agent to which said cancer cells are resistant.

8. The method according to claim 7 wherein the chemotherapeutic agent is selected from the group consisting of mitoxantrone, doxorubicin, and topotecan.

9. The method according to claim 7 wherein the chemosensitizing reversal agent is administered prior to, concurrently with, or after administration of the chemotherapeutic agent.

* * * * *